United States Patent
Jalali et al.

(10) Patent No.: US 11,768,191 B2
(45) Date of Patent: Sep. 26, 2023

(54) METHODS AND SYSTEMS FOR ESTIMATION OF OIL FORMATION VOLUME FACTOR

(71) Applicant: Schlumberger Technology Corporation, Sugar Land, TX (US)

(72) Inventors: Younes Jalali, Houston, TX (US); Ryota Tonoue, Kanagawa-ken (JP); Hua Chen, Sugar Land, TX (US); Christopher Harrison, Auburndale, MA (US); Kamal Kader, Tokyo (JP); Youxiang Zuo, Burnaby (CA); Adriaan Gisolf, Bucharest (RO); Cosan Ayan, Istanbul (TR); Michael Mallari Toribio, Manila (PH); Chetankumar Natwarlal Desai, Sugar Land, TX (US); Oliver Clinton Mullins, Houston, TX (US); Matthew T. Sullivan, Westwood, MA (US); Elizabeth Smythe, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 83 days.

(21) Appl. No.: 17/319,857

(22) Filed: May 13, 2021

(65) Prior Publication Data

US 2021/0263008 A1  Aug. 26, 2021

Related U.S. Application Data

(60) Continuation-in-part of application No. 16/531,640, filed on Aug. 5, 2019, now Pat. No. 11,187,693,
(Continued)

(51) Int. Cl.
   *G01N 33/28*  (2006.01)
   *E21B 47/06*  (2012.01)
   (Continued)

(52) U.S. Cl.
   CPC .......... *G01N 33/2823* (2013.01); *E21B 47/00* (2013.01); *E21B 47/06* (2013.01);
   (Continued)

(58) Field of Classification Search
   CPC ...... E21B 47/06; E21B 49/005; E21B 49/087; E21B 49/088; E21B 49/0875
   See application file for complete search history.

(56) References Cited

U.S. PATENT DOCUMENTS 4,599,117 A  7/1986  Luxemburg
4,646,083 A  2/1987  Woods
(Continued)

FOREIGN PATENT DOCUMENTS

| MX | 2011003898 A | 5/2011 |
| WO | 2010120285 A1 | 10/2010 |
| WO | 2019099770 A1 | 5/2019 |

OTHER PUBLICATIONS

MacMillan, D.J., Ginley, G.M., Dembicki Jr., H., "How to Obtain Reservoir Fluid Properties from An Oil Sample Contaminated with Synthetic Drilling Mud", SPE 38852 presented at SPE ATCE, San Antonio, TX, Oct. 5-8, 1997.
(Continued)

*Primary Examiner* — David Carroll
(74) *Attorney, Agent, or Firm* — Trevor G. Grove

(57) ABSTRACT

Embodiments of the disclosure can include systems, methods, and devices for determining saturation pressure of an uncontaminated fluid. A technique facilitates fluid analysis in situ at a downhole location. Downhole saturation pressure measurements and downhole OBM filtrate contamination of
(Continued)

a contaminated fluid may be obtained and a relationship may be determined between the saturation pressure measurements and OBM filtrate contamination. The relationship may be extrapolated to zero OBM filtrate contamination to determine the saturation pressure of the uncontaminated fluid. According to an embodiment, a sample of oil is obtained at the downhole location from oil in a reservoir. A downhole sampling system is used to determine whether a sample has contamination and other selected characteristics of the sample. The data obtained may be processed to provide a formation volume factor of the oil.

18 Claims, 15 Drawing Sheets

Related U.S. Application Data which is a division of application No. 14/535,199, filed on Nov. 6, 2014, now Pat. No. 10,371,690, application No. 17/319,857 is a continuation-in-part of application No. 15/810,298, filed on Nov. 13, 2017, now abandoned.

(51) Int. Cl.
| | |
|---|---|
| E21B 49/00 | (2006.01) |
| E21B 49/08 | (2006.01) |
| G01N 7/00 | (2006.01) |
| E21B 47/00 | (2012.01) |
| G01N 21/31 | (2006.01) |

(52) U.S. Cl.
CPC ............ *E21B 49/005* (2013.01); *E21B 49/08* (2013.01); *G01N 7/00* (2013.01); *G01N 21/31* (2013.01)

(56) References Cited

U.S. PATENT DOCUMENTS

| | | | |
|---|---|---|---|
| 5,473,939 A * | 12/1995 | Leder | G01N 7/14 73/152.52 |
| 6,178,815 B1 * | 1/2001 | Felling | E21B 49/10 73/152.19 |
| 6,881,349 B2 | 4/2005 | Mueller | |
| 6,956,204 B2 | 10/2005 | Dong et al. | |
| 6,994,164 B2 | 2/2006 | Tare et al. | |
| 7,081,615 B2 | 7/2006 | Betancourt et al. | |
| 7,372,264 B2 | 5/2008 | Akkurt et al. | |
| 8,024,125 B2 | 9/2011 | Hsu et al. | |
| 8,174,262 B2 | 5/2012 | Fransson et al. | |
| 8,909,478 B2 | 12/2014 | Ikeda et al. | |
| 9,051,822 B2 | 6/2015 | Ayan et al. | |
| 9,410,071 B1 | 8/2016 | Jiang et al. | |
| 9,557,312 B2 | 1/2017 | Zuo et al. | |
| 10,309,885 B2 | 6/2019 | Zuo et al. | |
| 10,316,655 B2 | 6/2019 | Zuo et al. | |
| 10,577,928 B2 | 3/2020 | Wang et al. | |
| 10,731,460 B2 | 8/2020 | Zuo et al. | |
| 10,746,019 B2 | 8/2020 | Indo et al. | |
| 2003/0158046 A1 | 8/2003 | Patel et al. | |
| 2004/0000905 A1 | 1/2004 | Freedman et al. | |
| 2004/0104341 A1 | 6/2004 | Betancourt et al. | |
| 2004/0149431 A1 | 8/2004 | Wylie et al. | |
| 2004/0193375 A1 * | 9/2004 | Dong | E21B 47/10 702/13 |
| 2005/0099618 A1 | 5/2005 | DiFoggio et al. | |
| 2007/0013911 A1 | 1/2007 | DiFoggio | |
| 2008/0156088 A1 | 7/2008 | Hsu et al. | |
| 2009/0078036 A1 * | 3/2009 | Terabayashi | E21B 49/081 73/152.55 |
| 2009/0192768 A1 | 7/2009 | Zuo et al. | |
| 2010/0277166 A1 | 11/2010 | Ramamoorthy et al. | |
| 2010/0311619 A1 | 12/2010 | Mettath et al. | |
| 2011/0088895 A1 * | 4/2011 | Pop | E21B 7/04 166/254.2 |
| 2011/0218736 A1 * | 9/2011 | Pelletier | E21B 49/081 702/12 |
| 2011/0284227 A1 | 11/2011 | Ayan et al. | |
| 2012/0018152 A1 | 1/2012 | van Zuilekom et al. | |
| 2012/0024523 A1 | 2/2012 | Ayan et al. | |
| 2013/0110402 A1 | 5/2013 | Godager | |
| 2013/0311099 A1 | 11/2013 | Eyuboglu et al. | |
| 2013/0340518 A1 | 12/2013 | Jones et al. | |
| 2014/0096957 A1 | 4/2014 | van Zuilekom et al. | |
| 2014/0116071 A1 | 5/2014 | Jung et al. | |
| 2014/0268156 A1 | 9/2014 | Smythe et al. | |
| 2014/0316705 A1 | 10/2014 | Zuo et al. | |
| 2014/0360257 A1 | 12/2014 | Indo et al. | |
| 2015/0000393 A1 | 1/2015 | Hernandez Marti et al. | |
| 2015/0013968 A1 | 1/2015 | Hsu et al. | |
| 2015/0142317 A1 | 5/2015 | Zuo et al. | |
| 2015/0211363 A1 | 7/2015 | Pop et al. | |
| 2015/0308261 A1 | 10/2015 | Zuo et al. | |
| 2015/0308264 A1 * | 10/2015 | Zuo | E21B 49/088 702/6 |
| 2015/0354345 A1 | 12/2015 | Meier et al. | |
| 2016/0061743 A1 | 3/2016 | Wang et al. | |
| 2016/0090836 A1 | 3/2016 | Wang et al. | |
| 2016/0131630 A1 | 5/2016 | Zuo et al. | |
| 2016/0319662 A1 | 11/2016 | Zuo et al. | |
| 2019/0145242 A1 | 5/2019 | Jalali et al. | |

OTHER PUBLICATIONS

Austad, T., Isom, T.P., "Compositional and PVT Properties of Reservoir Fluids Contaminated by Drilling Fluid Filtrate", Journal of Petroleum Science and Engineering, 20, 213-244 (2001).

Gozalpour, F., Danesh, A., Tehrani, D.-H., Todd, A.C, and Tohidi, B., "Predicting Reservoir Fluid Phase and Volumetric behavior from Samples Contaminated with Oil-Based Mud", SPE Reservoir Evaluation & Engineering, June, 197-205(2002).

Hy-Billiot, J., Bickert, J., Montel, F., Segalini, G., "Getting the Best from Formation Tester Sampling", SPE 77771 presented at SPE ATCE, San Antonio, Texas, Sep. 29-Oct. 2, 2002.

O'Keefe, M., Eriksen, K.O., Williams, S., Stensland, D., Vasques, R., "Focused Sampling of Reservoir Fluids Achieves Undetectable Levels of Contamination", SPE 101084 presented at SPE Asia Pacific Oil and Gas Conference and Exhibition, Adelaide, Australia, Sep. 11-13, 2006.

International Search Report and Written Opinion issued in the related PCT application PCT/US2015/056698 (IS13.4053-WO-PCT), dated Feb. 9, 2016.

International Preliminary Report on Patentability issued in the related PCT application PCT/US2015/056698 (IS13.4053-WO-PCT), dated May 5, 2017 (8 pages).

F.B. Thomas, Deconvolution of Drilling Fluid-Contaminated Oil Samples, 2002, 20 pages.

Mahmood Amani, Comparative Study of Using Oil-based Mud Versus Water based Mud in HPHT Fields, vol. 4, No. 2, 2012, pp. 18-27.

Definition of "Uncontaminated", Nov. 30, 2018, 1 page.

P.M. Dranchuk, J.H. Abou-Kassem, "Calculation of Z Factors for Natural Gases Using Equations of State", J. of Canadian Pet. Tech, Jul.-Sep. 1975, pp. 35-37.

K. E. Brown, "The Technology of Artificial Lift Methods", 1977, vol. 1, p. 86, (15 pages).

W.D. McCain Jr, "The Properties of Pet. Fluids", 2nd edition, 1990, p. 297 (63 pages).

Notice of Allowance issued in U.S. Appl. No. 16/531,640 dated Jul. 29, 2021, 19 pages.

Notice of Allowance issued in U.S. Appl. No. 17/533,158 dated Feb. 23, 2023, 35 pages.

Supplemental Notice of Allowability issued in U.S. Appl. No. 17/533,158 dated Apr. 19, 2023, 8 pages.

\* cited by examiner

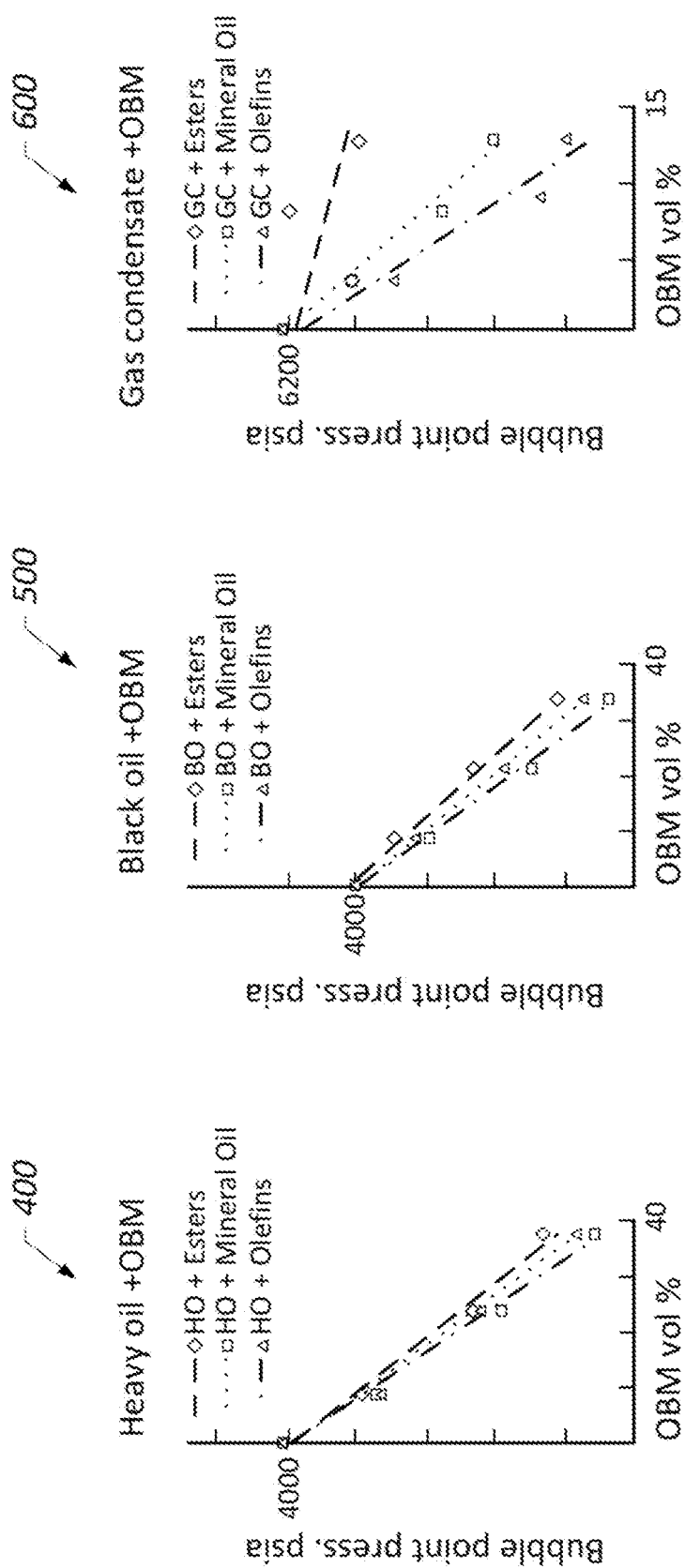

METHODS AND SYSTEMS FOR ESTIMATION OF OIL FORMATION VOLUME FACTOR

CROSS-REFERENCE TO RELATED APPLICATIONS

This application is a continuation-in-part application of co-pending U.S. patent application Ser. No. 16/531,640, entitled: "Methods and Systems for Correction of Oil-Based Mud Filtrate Contamination on Saturation Pressure," filed on Aug. 5, 2019, which is a divisional application of then co-pending U.S. patent application Ser. No. 14/535,199, entitled: "Methods and Systems for Correction of Oil-Based Mud Filtrate Contamination on Saturation Pressure," filed on Nov. 6, 2014, and granted as U.S. Pat. No. 10,371,690; this application is also a continuation-in-part application of co-pending U.S. patent application Ser. No. 15/810,298, entitled: "System and Methodology for Estimation of Oil Formation Volume Factor," filed on Nov. 13, 2017; the entirety of all of above are incorporated herein by reference.

BACKGROUND

Hydrocarbon fluids such as oil and natural gas are obtained from a subterranean geologic formation, referred to as a reservoir, by drilling a well that penetrates the hydrocarbon-bearing geologic formation. After a wellbore is drilled, various forms of well completion components may be installed to enable control over and to enhance efficiency of producing fluids from the reservoir. In many applications, fluid samples are taken along the wellbore to determine characteristics of the hydrocarbon fluid contained in the reservoir. The fluid samples may be tested to determine various characteristics of both the fluid and the reservoir, which can be useful in optimizing production from the reservoir. Some testing is performed downhole while other samples are retrieved to the surface for laboratory analysis.

This disclosure relates to determination of fluid properties using downhole fluid analysis (DFA). Fluid properties like gas-oil ratio (GOR), density, optical density (OD), composition, and others may be measured, detected, and/or estimated for fluids downhole in a well. Oil-based drilling mud (OBM) filtrate contamination may affect the fluid properties measured downhole, and obtaining fluid samples having zero OBM filtrate contamination may be difficult. The accuracy of such fluid properties may affect reservoir development, production, and management.

SUMMARY

A summary of certain embodiments disclosed herein is set forth below.

It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In general, a methodology and system are provided to facilitate fluid analysis in situ at a downhole location. According to an embodiment, a sample of oil is obtained from a reservoir at the downhole location in a borehole. A downhole sampling system is used to determine contamination of the sample of oil and to determine other selected characteristics of the sample. The data obtained is then processed to provide a formation volume factor of the sample of oil. The sample analysis may be performed at selected stations along the borehole to facilitate rapid development of a realistic model of fluid distribution and property variation in the reservoir, thus enabling an improved oil recovery strategy.

Embodiments of this disclosure relate to various methods and systems for correction of oil-based mud filtrate contamination on saturation pressure. In particular, certain embodiments of the disclosure can include methods and systems for determining saturation pressure of an uncontaminated fluid. According to some embodiments, a method is provided that can include obtaining, by using at least one property of a contaminated fluid measured downhole by a downhole tool, oil-based mud (OBM) filtrate contamination of the contaminated fluid. The contaminated fluid includes uncontaminated fluid and the OBM filtrate. The method can further include obtaining downhole saturation pressure measurements of the reservoir fluid and determining a relationship between the downhole saturation pressure measurements and the OBM filtrate contamination. The method can also include extrapolating the determined relationship between the downhole saturation pressure measurements and the OBM filtrate contamination to a zero OBM filtrate contamination and determining a saturation pressure of the uncontaminated fluid at the zero OBM filtrate contamination.

According to an embodiment, a method for downhole fluid analysis is provided that can include deploying a sampling system downhole in a borehole located within a reservoir containing hydrocarbons. The method can further include using the sampling system to obtain fluid samples at a plurality of stations along the borehole, the fluid samples containing uncontaminated fluid and oil based mud (OBM) filtrate. The method can further include providing a processor with at least one property of the fluid samples and analyzing each fluid sample in situ to determine saturation pressure and density of each contaminated fluid sample. The method can further include correcting for any contamination and determining the saturation pressure of each uncontaminated fluid sample. The method can also include determining a formation volume factor (FVF) of oil in the reservoir based on saturation pressure and density of the uncontaminated fluid.

According to an embodiment, a method can include obtaining a fluid sample from a reservoir at a downhole location in a borehole, the fluid sample containing uncontaminated fluid and oil based mud filtrate. The method can further include providing a processor with at least one property of the fluid sample, and using a contamination monitoring module and sensors at the downhole location to obtain data on the uncontaminated fluid. The method can also include processing the data obtained downhole to determine an FVF of oil in the reservoir.

According to an embodiment, a system is provided that can include a well string comprising a sampling system deployed downhole in a wellbore, the sampling system comprising a contamination monitoring module. The system can further include a processor configured to process the data, and a non-transitory tangible machine-readable memory coupled to the processor, the non-transitory tangible machine-readable memory storing machine-readable instructions that when executed by the processor cause the processor to perform operations. The operations can include measuring downhole saturation pressures of a contaminated fluid over a pumpout volume or a pumpout time, wherein the contaminated fluid comprises uncontaminated fluid and OBM filtrate. The operations can further include determining a function for the measured saturation pressures based on the pumpout volume or pumpout time, and extrapolating the function to infinite pumpout volume or infinite pumpout time. The operations can further include determining a saturation pressure for the uncontaminated fluid at the infinite pumping volume or infinite pumping time, and obtaining a saturation pressure of the uncontaminated fluid. Additionally, the downhole saturation pressure comprises bubble point pressures. Further, the operations may further include determining the FVF of the uncontaminated fluid based on the downhole saturation pressure and a density of the uncontaminated fluid.

According to an embodiment, a system is provided that can include a downhole tool operable within a wellbore extending into a subterranean formation, a controller coupled to the downhole tool, and a non-transitory tangible machine-readable memory coupled to a processor of the controller. The non-transitory tangible machine-readable memory stores machine-readable instructions that when executed by the processor cause the processor to perform operations that can include obtaining, by using at least one property of a contaminated fluid measured downhole by a downhole tool, oil-based mud (OBM) filtrate contamination of the contaminated fluid. The contaminated fluid can include uncontaminated fluid and the OBM filtrate. Additionally, the non-transitory tangible machine-readable memory stores machine-readable instructions that when executed by the processor cause the processor to perform operations that can further include obtaining downhole saturation pressure measurements of the reservoir fluid and determining a relationship between the downhole saturation pressure measurements and the OBM filtrate contamination. The non-transitory tangible machine-readable memory also stores machine-readable instructions that when executed by the processor cause the processor to perform operations that can include extrapolating the determined relationship between the downhole saturation pressure measurements and the OBM filtrate contamination to a zero OBM filtrate contamination and determining a saturation pressure of the uncontaminated fluid at the zero OBM filtrate contamination.

Further, embodiments of this disclosure relate to various methods and systems for determining OBM filtrate contamination of a contaminated fluid. According to some embodiments, a method is provided that can include measuring downhole saturation pressures of a contaminated fluid over a pumpout volume or a pumpout time, the contaminated fluid including uncontaminated fluid and an OBM filtrate. The method can further include determining a function for the measured saturation pressures based on the pumpout volume or pumpout time and extrapolating the function to infinite pumpout volume or infinite pumpout time. Additionally, the method can include determining a saturation pressure for the uncontaminated fluid at the infinite pumping volume or infinite pumping time and obtaining a saturation pressure of the OBM filtrate. The method can also include determining an OBM filtrate contamination of the contaminated fluid based on the saturation pressure for the uncontaminated fluid, the saturation pressure for the OBM filtrate, and the measured saturation pressure for the contaminated fluid.

According to another embodiment, a system is provided that includes a downhole tool operable within a wellbore extending into a subterranean formation, a controller coupled to the downhole tool, and a non-transitory tangible machine-readable memory coupled to a processor of the controller. The non-transitory tangible machine-readable memory stores machine-readable instructions that when executed by the processor cause the processor to perform operations that can include measuring downhole saturation pressures of a contaminated fluid over a pumpout volume or a pumpout time, the contaminated fluid including uncontaminated fluid and an OBM filtrate. Additionally, the non-transitory tangible machine-readable memory stores machine-readable instructions that when executed by the processor cause the processor to perform operations that can further include further includes determining a function for the measured saturation pressures based on the pumpout volume or pumpout time and extrapolating the function to infinite pumpout volume or infinite pumpout time. The non-transitory tangible machine-readable memory stores machine-readable instructions that when executed by the processor cause the processor to perform operations that can further include determining a saturation pressure for the uncontaminated fluid at the infinite pumping volume or infinite pumping time and obtaining a saturation pressure of the OBM filtrate. Further, the non-transitory tangible machine-readable memory stores machine-readable instructions that when executed by the processor cause the processor to perform operations that can further include determining an OBM filtrate contamination of the contaminated fluid based on the saturation pressure for the uncontaminated fluid, the saturation pressure for the OBM filtrate, and the measured saturation pressure for the contaminated fluid.

Various refinements of the features noted above may be undertaken in relation to various aspects of the present disclosure. Further features may also be incorporated in these various aspects as well. These refinements and additional features may be determined individually or in any combination. For instance, various features discussed below in relation to the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which:

FIGS. 10-12 are plots of saturation pressure vs. OBM filtrate contamination in accordance with an embodiment of the present disclosure;

DETAILED DESCRIPTION

Figure 1:
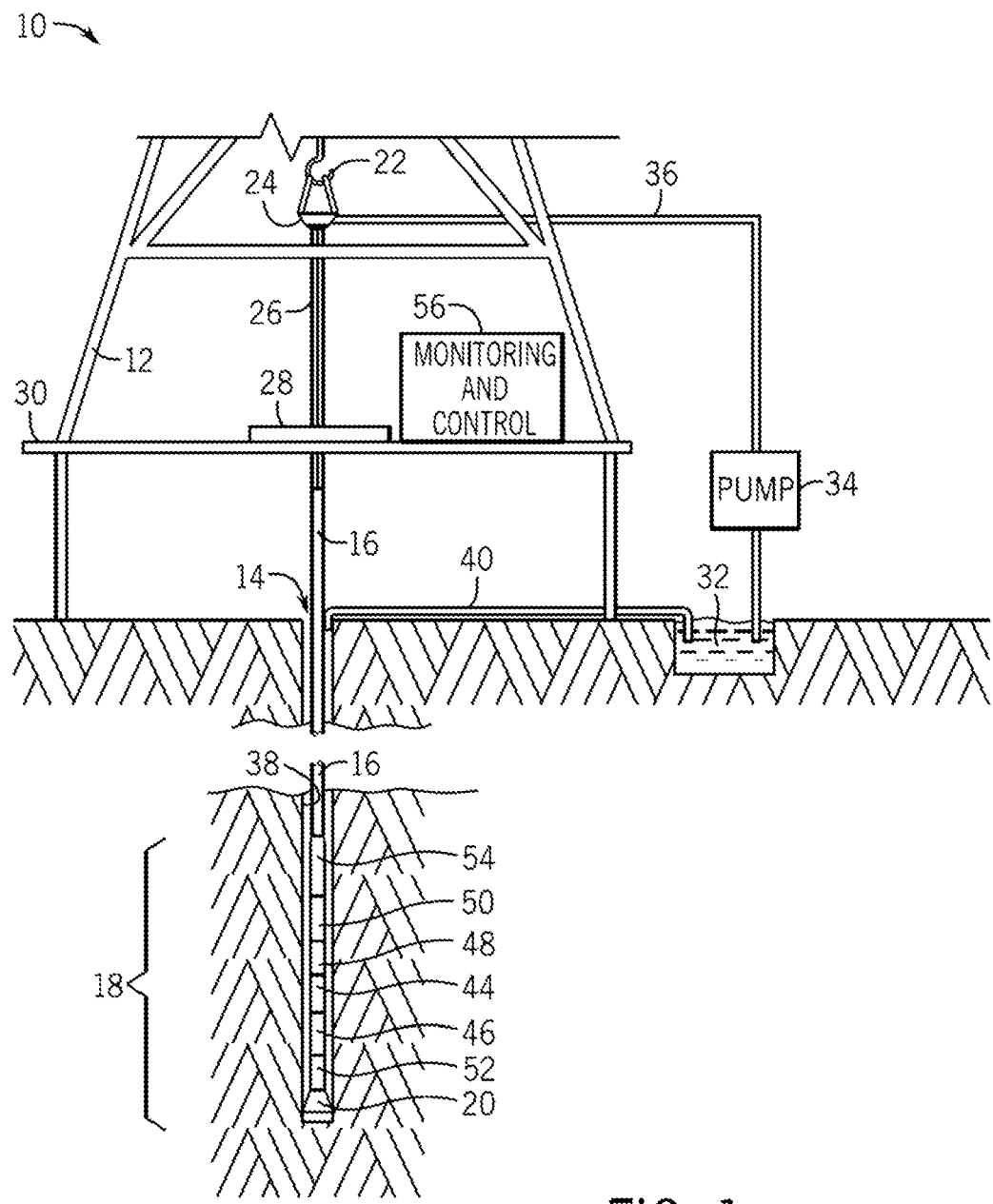
FIG. 1 generally depicts a drilling system having a fluid sampling tool in a drill string in accordance with an embodiment of the present disclosure.

Described herein are various embodiments related to the determination of saturation pressure of an uncontaminated fluid using downhole saturation pressure measurements of a contaminated fluid and OBM filtrate contamination. As used herein, the saturation pressure may refer to a dew point pressure or a bubble point pressure. In some embodiments, downhole OBM filtrate contamination and downhole saturation pressure measurements of a contaminated fluid may be obtained. In some embodiments, a regression (e.g., a linear regression) may be performed on a plot of downhole saturation pressure measurements vs. OBM filtrate contamination to determine a linear function. The function (e.g., a linear function) may be extrapolated to zero OBM filtrate contamination to determine the saturation pressure (bubble point pressure or dew point pressure) of the uncontaminated fluid. With the recent advances of sampling technology and platforms, very low contamination samples can be obtained after a reasonable pumping time. In this case, the near-zero contamination fluids obtained can be measured directly to determine the saturation pressure and density of the uncontaminated fluid.

Also described herein are embodiments related to the determination of OBM filtrate contamination from downhole saturation pressure measurements. In some embodiments, downhole saturation pressure, such as bubble point pressures, may be measured during a pumpout volume or time. A function (e.g., a power function) for the saturation pressure vs. pumpout volume or time may be fitted, and the function may be extrapolated to infinite volume or infinite time to obtain a bubble point pressure for the uncontaminated fluid. The OBM filtrate saturation pressure may also be obtained. The OBM filtrate contamination may be determined using the saturation pressure for the uncontaminated fluid, the saturation pressure for the OBM filtrate, and the measured saturation pressure for the contaminated fluid.

The sampling system may be deployed downhole into a borehole (e.g., wellbore, as part of a well string). By way of example, the sampling system may be deployed downhole via tubing, wireline, or another suitable conveyance. According to embodiments, the sampling system is employed for downhole fluid analysis during wireline operations, while-drilling operations, or other suitable downhole operations.

In general, the sampling system may be used to obtain measurements in situ for downhole fluid analysis so as to obtain desired physical properties of reservoir fluid (e.g., physical properties that would otherwise be determined via laboratory procedures). As described in greater detail below, a desired physical property of the reservoir fluid that may be obtained via the sampling system is the formation volume factor (FVF). The FVF is the volume occupied by live oil in the reservoir which, upon production and crude separation/stabilization processes, yields one barrel of dead or degassed oil in a stock tank. Values of FVF may vary between, for example, 1.05 and 2.7 reservoir barrels per stock tank barrel.

One of the uses of this FVF property is to determine the original oil-in-place in a geological structure in terms of stock tank barrels. However, FVF also may be used to estimate the fraction of oil-in-place, which would be recoverable via various recovery methods. Consequently, knowledge regarding FVF can have a direct impact on evaluation of reservoirs, production techniques, and recovery of hydrocarbons.

Traditionally, flashing of live oil samples in the laboratory was used to obtain certain physical properties of crude oil systems. The downhole sampling system described herein, however, enables the FVF to be obtained downhole and to be determined for a plurality of different stations (e.g., different stations/locations along the borehole). The FVF/property can be determined during an in situ fluid analysis job, which may use stations where samples are taken and stations were samples are not taken. With knowledge obtained immediately from the analysis of downhole oil samples, an operator is able to develop a more realistic model of the fluid distribution and property variation (e.g., FVF variation) in the reservoir. This knowledge/model may be used to plan a more differentiated and efficient hydrocarbon recovery strategy.

As described in greater detail below, the downhole sampling system enables a methodology that uses measurements of in situ fluid analysis such as downhole spectroscopy for estimation of composition and gassiness of crude oil. The methodology also may employ measurements based on incipient flashing (not full flash to atmospheric, which may not be feasible downhole, but flashing to a bubble point pressure). The downhole sensor system may utilize a microfluidic measurement module having a depressurization chamber to determine, for example, bubble point pressure and density of the sample fluid. By using these various measurements, the FVF of the oil sample may be obtained as well as the FVF variation from initial reservoir pressure to bubble point pressure (and even below bubble point pressure) during a reservoir pressure depletion process.

These and other embodiments of the disclosure will be described in more detail through reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

More specifically, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 can include a drilling rig 12 positioned over a well 14. Although depicted as an onshore drilling system 10, it is noted that the drilling system could instead be an offshore drilling system. The drilling rig 12 can support a drill string 16 that includes a bottomhole assembly 18 having a drill bit 20. The drilling rig 12 can rotate the drill string 16 (and its drill bit 20) to drill the well 14.

The drill string 16 can be suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 can be coupled to the drill string 16, and the swivel 24 can allow the kelly 26 and the drill string 16 to rotate with respect to the hook 22. In the presently illustrated embodiment, a rotary table 28 on a drill floor 30 of the drilling rig 12 can be constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 can be circulated through the well 14 by a pump 34. The drilling fluid 32 can be pumped from a mud pit (or some other reservoir, such as a mud tank) into the drill string 16 through a supply conduit 36, the swivel 24, and the kelly 26. The drilling fluid 32 can exit near the bottom of the drill string 16 (e.g., at the drill bit 20) and can return to the surface through the annulus 38 between the wellbore and the drill string 16. A return conduit 40 can transmit the returning drilling fluid 32 away from the well 14. In some embodiments, the returning drilling fluid 32 can be cleansed (e.g., via one or more shale shakers, desanders, or desilters) and reused in the well 14. The drilling fluid 32 may include an oil-based mud (OBM) that may include synthetic muds, diesel-based muds, or other suitable muds.

In addition to the drill bit 20, the bottomhole assembly 18 can also include various instruments that measure information of interest within the well 14. For example, as depicted in FIG. 1, the bottomhole assembly 18 can include a logging-while-drilling (LWD) module 44 and a measurement-while-drilling (MWD) module 46. Both modules can include sensors, housed in drill collars, that can collect data and enable the creation of measurement logs in real-time during a drilling operation. The modules could also include memory devices for storing the measured data. The LWD module 44 can include sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 can include sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in detail below, one or more of the modules 44, 46, and 48 can be or can include a fluid sampling tool configured to obtain a sample of a fluid from a subterranean formation and perform downhole fluid analysis to measure various properties of the sampled fluid. These properties may include an estimated density and/or optical density of the OBM filtrate, the sampled fluid, and other fluids. These and other estimated properties may be determined within or communicated to the LWD module 44, such as for subsequent utilization as input to various control functions and/or data logs.

The bottomhole assembly 18 can also include other modules. As depicted in FIG. 1 by way of example, such other modules can include a power module 50, a steering module 52, and a communication module 54. In one embodiment, the power module 50 can include a generator (such as a turbine) driven by flow of drilling mud through the drill string 16. In other embodiments, the power module 50 could also or instead include other forms of power storage or generation, such as batteries or fuel cells. The steering module 52 may include a rotary-steerable system that facilitates directional drilling of the well 14. The communication module 54 can enable communication of data (e.g., data collected by the LWD module 44 and the MWD module 46) between the bottomhole assembly 18 and the surface. In one embodiment, the communication module 54 can communicate via mud pulse telemetry, in which the communication module 54 uses the drilling fluid 32 in the drill string as a propagation medium for a pressure wave encoding the data to be transmitted.

The drilling system 10 can also include a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
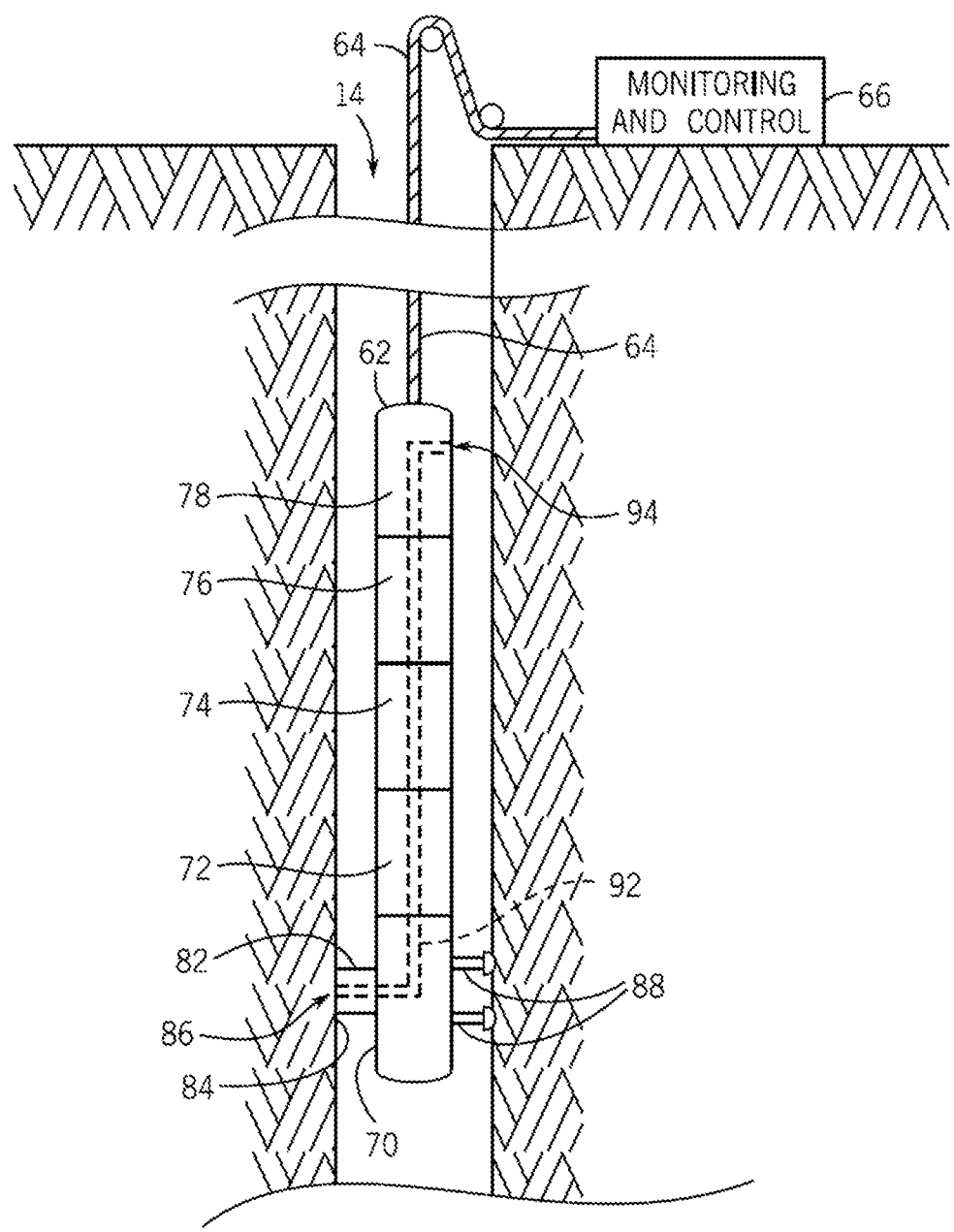
FIG. 2 generally depicts a fluid sampling tool deployed within a well on a wireline in accordance with an embodiment of the present disclosure.

Another example of using a downhole tool for formation testing within the well 14 is depicted in FIG. 2. In this embodiment, a fluid sampling tool 62 can be suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 can control movement of the fluid sampling tool 62 within the well 14 and can receive data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) can be incorporated into or as one or more modules of the bottomhole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 can include a probe 82 that may be extended (e.g., hydraulically driven) and pressed into engagement against a wall 84 of the well 14 to draw fluid from a formation into the fluid sampling tool 62 through an intake 86. As depicted, the probe module 70 can also include one or more setting pistons 88 that may be extended outwardly to engage the wall 84 and push the end face of the probe 82 against another portion of the wall 84. In some embodiments, the probe 82 can include a sealing element or packer that isolates the intake 86 from the rest of the wellbore. In other embodiments, the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 can draw the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72, which may also be referred to as the fluid analyzer 72 or a DFA module, can include one or more sensors for measuring properties of the sampled formation fluid, such as the optical density of the fluid, and the power module 76 provides power to electronic components of the fluid sampling tool 62. In some embodiments, the fluid analysis module 72 may include a downhole pressure-volume-temperature PVT unit and may obtain microfluidic measurements. In such embodiments, the fluid analysis module 72 may be referred to as a DFA microfluidics module. The measurements may be utilized to estimate a formation volume factor of the contaminated formation fluid, as well as density, optical density, GOR, compressibility, saturation pressure, viscosity, and/or mass fractions of compositional components of the contaminated formation fluid and/or contaminants therein (e.g., OBM filtrate), among others.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
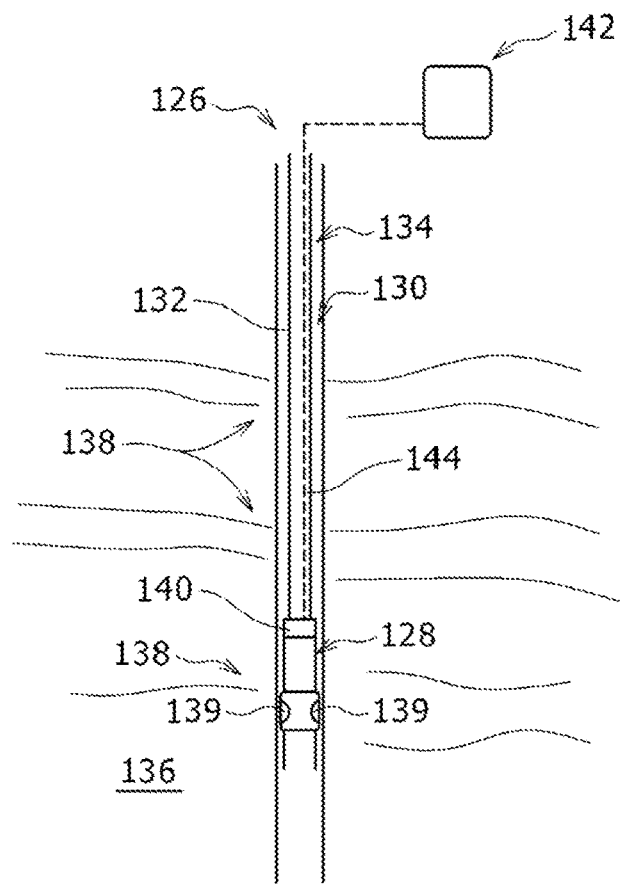
FIG. 3 is a schematic illustration of an example of a well system comprising a sampling system deployed downhole in a borehole, according to an embodiment of the disclosure.

Referring generally to FIG. 3, an example of a well system 126 is illustrated. In this embodiment, the well system 126 comprises a sampling system 128, which may be conveyed downhole into a borehole 130 (e.g., a wellbore), via a conveyance 132. The conveyance 132 may comprise tubing (e.g., production tubing or coiled tubing), wireline, or another suitable conveyance.

Additionally, the sampling system 128 and conveyance 132 may be part of an overall well string 134 having various other components selected for a given operation. For example, the well string 134 may comprise a drill string and sampling system 128 may be used to obtain well fluid samples (e.g., oil samples), during a drilling operation. The well string 134 also may be used during a wireline operation in wellbore 130 or during other types of well operations.

The sampling system 128 is moved to a desired location along borehole 130 so as to obtain a sample of fluid (e.g., oil), which enters borehole 130 from a reservoir 136 in the surrounding subterranean geologic formation. In various applications, the sampling system 128 may be moved via conveyance 132 to a plurality of different stations 138 along borehole 130 for analysis of a given fluid sample or samples. The fluid samples (e.g., oil samples), may be taken at selected stations 138 for in situ analysis at the downhole location. The sampling system 128 may comprise or work in cooperation with PVT (pressure/volume/temperature) sensors 139 (e.g., pressure and temperature sensors), to monitor pressures and temperatures at the various formation stations 138.

The data obtained via the in situ analysis by sampling system 128 may be processed further to determine the desired well fluid/oil property (e.g., FVF). Processing of the data may be performed downhole, at the surface, or partially downhole and partially at the surface. In some applications, the processing may be done at least in part via a downhole processor 140 operatively coupled with sampling system 128. The sampling system 28 also may be coupled with a surface processing system 142 via a suitable telemetry system 144 (e.g., a wired or wireless telemetry system). In some applications, both the downhole processor 140 and the surface processing system 142 may be utilized in processing data obtained via the in situ analysis performed by downhole sampling system 128.

Figure 4:
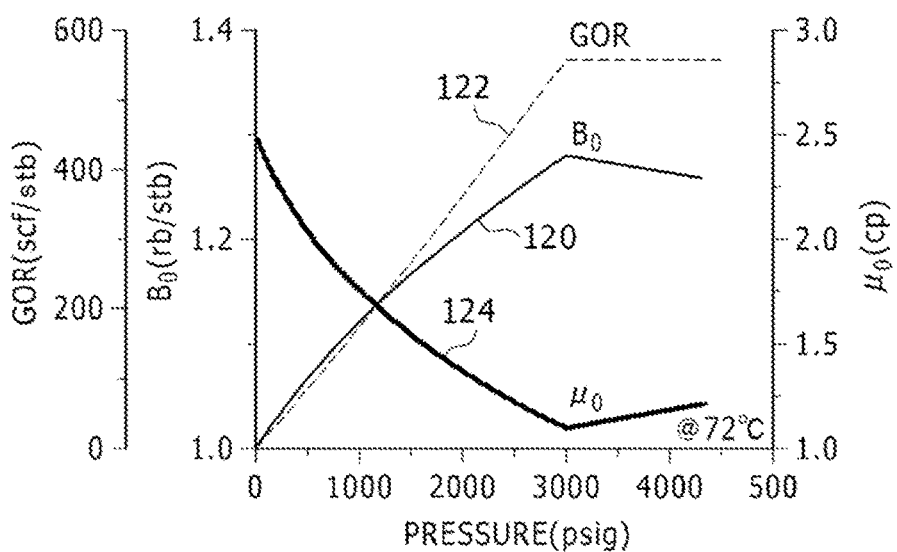
FIG. 4 is a graphical illustration showing formation volume factor behavior versus reservoir pressure, according to an embodiment of the disclosure.

Referring generally to FIG. 4, a graphical example is provided, which illustrates FVF behavior of a sample of oil (shown as Bo in the graph plot) versus reservoir pressure. In this example, a graph line 120 illustrates changes in FVF of the sample of oil as pressure changes from an initial pressure of about 4400 psi to a bubble point pressure of about 3000 psi to atmospheric pressure. As illustrated by the graph, the FVF(Bo) peaks at approximately 1.27 reservoir barrels per stock tank barrel (RB/STB) at the bubble point pressure.

A negative slope of the Bo graph line 120 at pressures above bubble point pressure indicates the crude oil in the sample is moderately compressible. At pressures below the bubble point pressure, the Bo graph line 120 tends toward unity. In the diagram illustrated, a graph line 122 is used to represent a gas to oil ratio (GOR) throughout the pressure range. Similarly, a graph line 124 is used to represent viscosity throughout the pressure range.

Figure 5:
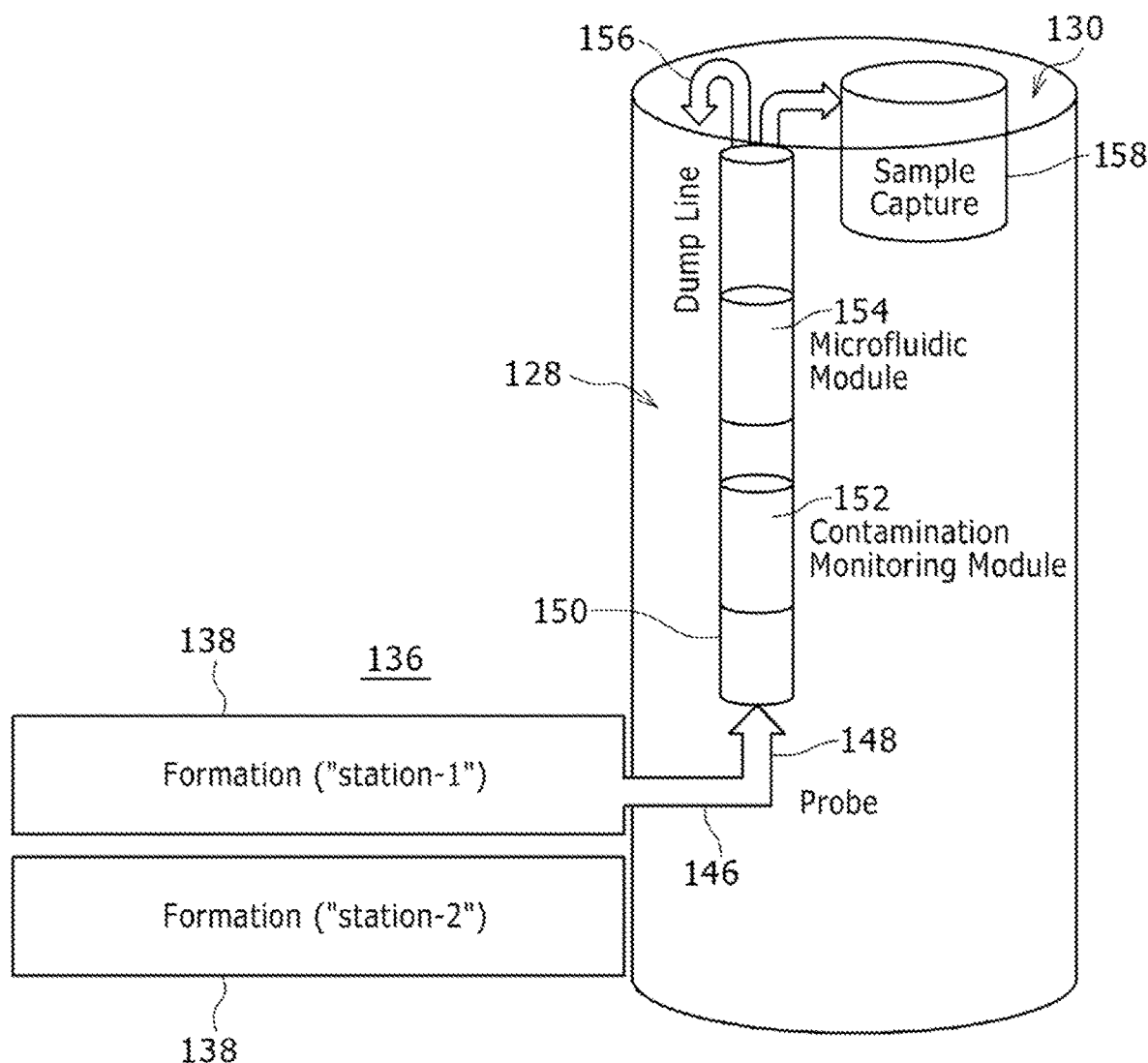
FIG. 5 is a schematic illustration of an example of a sampling system for testing fluid samples in situ within the borehole, according to an embodiment of the disclosure.

Referring generally to FIG. 5, an example of sampling system 128 is illustrated. In this embodiment, sampling system 128 is deployed in wellbore 130 proximate the first formation station 138 of a plurality of stations 138. The sampling system 128 comprises a probe 146 through which a sample of fluid 148 (e.g., a sample of oil), is drawn from the surrounding formation/reservoir 136. The sample 148 flows into a sampling system structure 150 (e.g., a housing or manifold), for analysis via appropriate fluid analysis modules.

The fluid analysis modules may be selected to, for example, analyze each sample 148 in situ to correct for contamination and to determine other sample characteristics, such as bubble point pressure and density. By way of example, the sampling system 128 may comprise a contamination monitoring module 152 and a microfluidic measurement module 154. In this example, each sample 148 flows through probe 146, into structure 150, and into contamination monitoring module 152 for in situ detection and correction due to contamination of the sample 148 (e.g., oil sample), so as to facilitate further analysis.

In the illustrated embodiment, the sample 148 continues to flow through structure 150 and into microfluidic measurement module 154. The microfluidic measurement module 154 is then used in situ to determine other desired characteristics (e.g., bubble point pressure and density), of the sample 148 so as to enable determination of the formation volume factor and/or other desired property via the data obtained from the downhole analysis. Data resulting from the analysis at contamination monitoring module 152 and microfluidic measurement module 154 may be provided to the processing system (e.g., downhole processor 140 and/or surface processing system 142), to determine the formation volume factor and/or other desired property. In the specific example illustrated, each sample 148 may be further directed through structure 150 and flowed into, for example, a dump line 156 and/or sample capture chamber 158.

Figure 6:
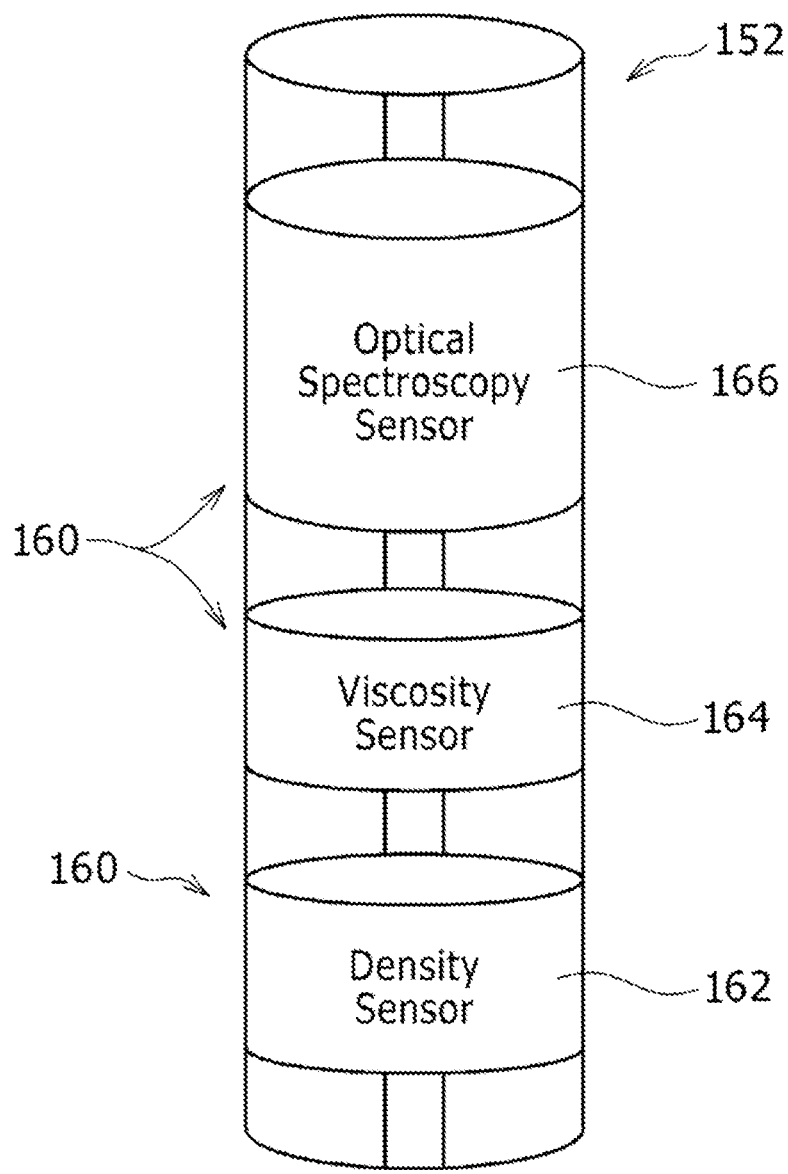
FIG. 6 is a schematic illustration of an example of a contamination monitoring module, which may be employed in the sampling system, according to an embodiment of the disclosure.
Figure 7:
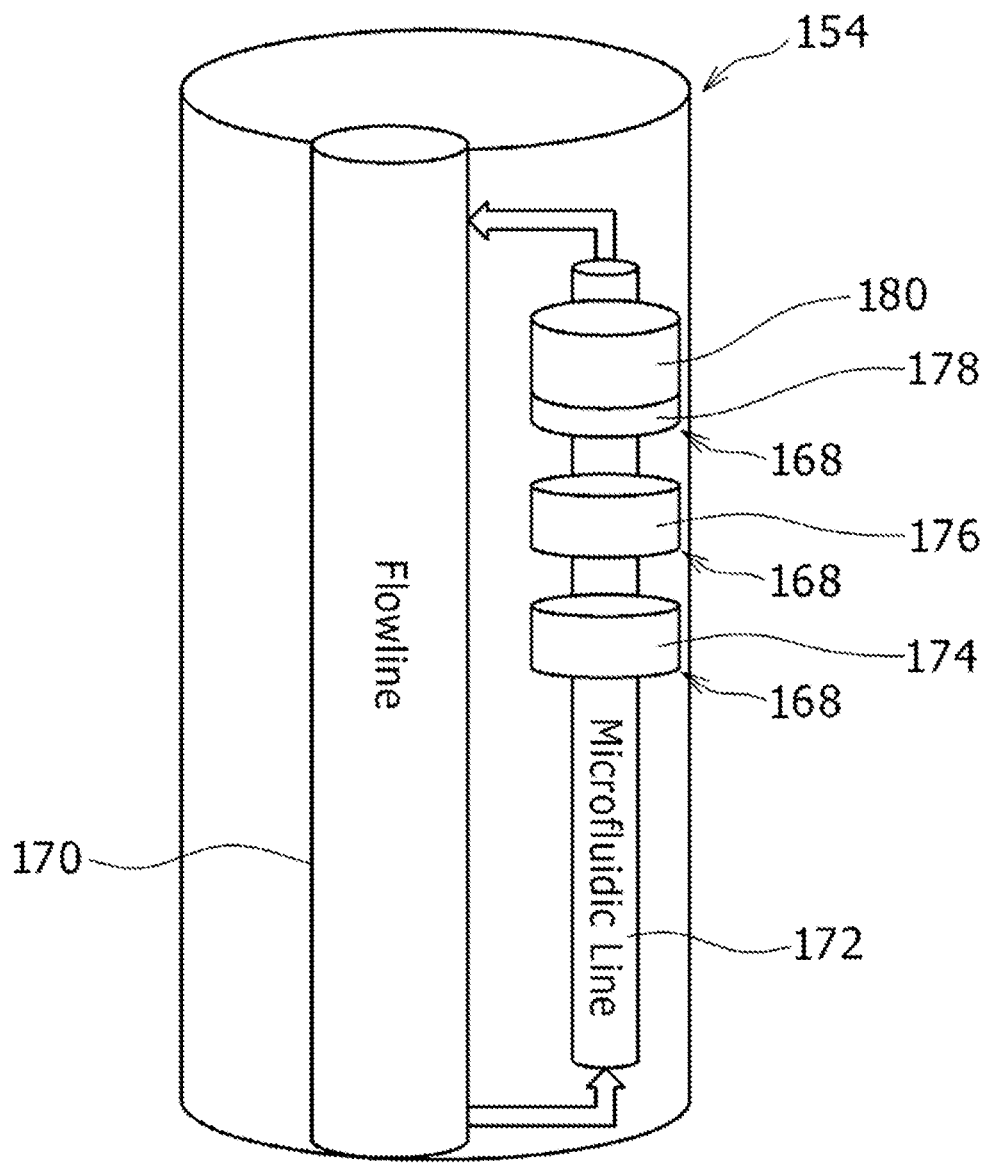
FIG. 7 is a schematic illustration of an example of a microfluidic module, which may be employed in the sampling system, according to an embodiment of the disclosure.

Referring generally to FIGS. 6 and 7, examples of contamination monitoring module 152 and microfluidic measurement module 154, respectively, are illustrated. As illustrated in FIG. 6, the contamination monitoring module 152 may comprise a plurality of sensors 160 arranged to detect specific characteristics of each sample 148 so as to provide data on contaminating constituents within the sample 148. By way of example, the contamination monitoring module 152 may comprise a density sensor 162, a viscosity sensor 164, and an optical spectroscopy sensor 166. These sensors 160 may be used individually or in combination to obtain data indicative of contaminants within the oil sample 148 (or other sample) obtained from the corresponding station 138. The contamination monitoring module 152 may be constructed for focused sampling (e.g., dual flowline sampling), or unfocused sampling (e.g., single flowline sampling). The embodiment illustrated shows the contamination monitoring module 152 as an unfocused sampling module with a single probe and single flowline but the module 152 may be constructed for more advanced monitoring via, for example, focused sampling with two probes and two flowlines.

As illustrated in FIG. 7, the microfluidic measurement module 154 also may comprise a variety of sensors 168 selected to obtain data that can be processed to, for example, determine the FVF of each sample 148 from selected formation stations 138. In the example illustrated, the microfluidic measurement module 154 comprises a primary flowline 170 and a microfluidic line 172 with sensors 168 disposed along the microfluidic line 172. By way of example, sensors 168 may comprise a density sensor 174, a viscosity sensor 176, and an optical spectroscopy sensor 178, which cooperate with a depressurization chamber 180. The depressurization chamber 180 may be operated to provide controlled depressurization of each sample 148 (e.g., to determine bubble point pressure), during collection of data for processing via the processing system 140 and/or 142. It should be noted that sensors 160 and/or 168 also may comprise pressure and temperature sensors 139 for monitoring downhole conditions. In some applications, the pressure and temperature sensor 139 may be separate from sampling system 128 but operatively coupled with downhole processor 140 and/or surface processing system 142.

As illustrated, the sample 148 (e.g., oil sample), flows from primary flowline 170, into microfluidic line 172, through sensors 168 and back into the primary flowline 170. Data obtained in situ via the flow of fluid samples through contamination monitoring module 152 and microfluidic module 154 of sampling system 128 may be processed to determine the FVF of the oil in the formation/reservoir 136. The data also may be used to determine changes in the FVF (e.g., variation of FVF over a reservoir pressure depletion cycle). A computational procedure for determining the FVF and desired changes in the FVF is provided below.

In implementing the computational procedure via, for example, downhole processor 140 and/or surface processing system 142, various common values are employed and oilfield units are used. For example, the computational procedure may be carried out with the following assumptions: standard pressure and temperature is considered 14.7 psi at 60° F. (520° R); water density at standard conditions is 62.37 lbs/ft$^3$ (this value may be used to obtain dead oil density from oil specific gravity or from API gravity, which in one embodiment of the computational procedure/algorithm is inferred from bubble point pressure of the oil sample 148 and other parameters); air density at standard conditions is 0.076 lb/ft$^3$; the universal gas constant is 10.73 psi·ft$^3$/lbmole.° Rankine; the molecular weight of air is 28.9 lb/lbmole; and one barrel is 5.615 ft$^3$.

According to this computational procedure, the volume of live oil in the reservoir (at bubble point pressure) is considered to be the sum of the volume of dead oil at bubble point pressure and the volume of dissolved gas at bubble point pressure (BPP), both at reservoir temperature. This provides the following expression in Equation 1:

$$Bob = \frac{dead.oil.vol(at.BPP.\ \&.reservoir.temp) + dissolved.gas.vol(at.BPP.\ \&.reservoir.temp)}{dead.oil.vol(stock.\text{tank})} \quad (1)$$

With respect to the term "Bob", the "B" is a term that represents the formation volume factor (FVF); the "o" indicates the formation volume factor is for oil; and the "b" indicates the formation volume factor is at the bubble point pressure. In other words, the term "Bob" refers to the starting point of the shrinkage process that results when live oil is brought from the reservoir 136 to the surface and stabilized in separation operations before being shipped to, for example, a sales line for delivery. The starting point of this shrinkage process is at the bubble point pressure which, for a virgin reservoir, is the lowest initial pressure encountered. The end point of this shrinkage process is when the oil is in a stock tank at a surface facility.

For purposes of the computational procedure, the dead oil volume at reservoir condition is assumed to be equal to the dead oil volume at stock tank condition. Therefore, we can assume the volume shrinkage caused by cooling of the virtual dead oil when moving from reservoir to stock tank condition is of the same order of magnitude as the volume expansion caused by the drop in pressure from bubble point pressure to atmospheric pressure. This assumption can be relaxed by introducing a tuning parameter (e.g., a minor or secondary tuning parameter), which allows the two dead oil volumes to not be identical. However, sufficient accuracy is achieved by assuming the quality of the two dead oil volumes at reservoir condition and stock tank condition. Consequently, the following expression described below in Equation 2 is obtained, which indicates that "Bob" is unity plus a correction that is a volume ratio of dissolved gas at bubble point pressure to dead oil:

$$Bob = 1 + \frac{dissolved.gas.vol.at.BPP}{dead.oil.vol} \quad (2)$$

The volume ratio in Equation 2 can be rewritten as the product of a mass ratio and density ratio as follows in Equation 3:

$$\frac{dissolved.gas.vol.at.BPP}{dead.oil.vol} = \frac{dissolved.gas.mass}{dead.oil.mass} \frac{dead.oil.density}{dissolved.gas.density.at.BPP} \quad (3)$$

The mass ratio can be determined from compositional information. However, because our compositional measurement is made in mass terms, the composition should be corrected for contamination. It should be noted that the computational procedure may utilize various contamination corrections, such as those described herein.

Referring again to FIGS. 5 and 6, the contamination monitoring module 152 is used to collect data that may be used to enable processing of the desired contamination corrections. Hydrocarbons may be categorized according to their carbon numbers that can range from C1 to C6 and above. As a first approximation when performing a contamination correction, an assumption may be made that C1-C4 hydrocarbons end up in the gas phase and C5+ hydrocarbons end up in the oil phase. The assumption is valid if the weight of the fraction of C1-C4 that ends up in the oil phase is equivalent to the weight fraction of C5+ that ends up in the gas phase (the so-called cross terms). Because real gas-oil partition may deviate from this assumption the assumption may be tuned by using a partition coefficient: Ki=yi/xi (yi is mole fraction of component i in the gas phase; xi is mole fraction of component i in the oil phase; Ki is a function of pressure (P) and temperature (T) and overall composition, which is represented by a "convergence pressure" or Pk). Use of the partition coefficient would be a refinement and may be used as a primary tuning parameter. For now, we will proceed with the assumption that C1-C4 escapes into the gas phase while C5+ condenses into the liquid phase. Therefore, the following equation described below in Equation 4 is obtained:

$$\frac{dissolved.gas.mass}{dead.oil.mass} = \frac{\sum_{i=1}^{4} wi}{1 - \sum_{i=1}^{4} wi}; \quad (4)$$

wi is weight fraction of component $i$

The dissolved gas density at bubble point pressure indicated in Equation 3 above may be obtained from the real gas law in lb/ft³ according to Equation 5 as follows:

$$dissolved.gas.density.at.BPP = \frac{BPP \times M}{Zb \times R \times Tres.° \text{ Rankine}} \quad (5)$$

Where:

R=10.73 psi·ft3/lbmole.° Rankine; gas constant in oilfield units;

Tres.° Rankine=Tres.° F.+460; reservoir temperature in degrees Rankine;

Zb=Zb(BPP,Tres,Composition); gas deviation factor at BPP; evaluated by Dranchuk method; (see "Calculations of Z Factors for Natural Gases Using Equations of State", P. M. Dranchuk, J. H. Abou-Kassem; J. of Canadian Pet. Tech, July-September 1975, pp. 35-37.);

$$M = \sum_{i=1}^{4} yi Mi;$$

gas molecular weight (Mi is molecular weight of each component; yi is mole fraction); and $$yi = \frac{wi/Mi}{\sum_{i=1}^{4} wi/Mi};$$

$i = 1,2,3,4$

In this computational procedure example, wi and BPP are contamination corrected values.

The dead oil density in Equation 3 above may be estimated via a suitable overall method (e.g., according to two independent methods). The two independent methods may be used to determine the spread in FVF of oil at bubble point pressure referred to herein as Bob. A first of the two independent methods may be expressed as follows by Equation 6:

$$dead.oil.density = \frac{GOR \times 14.7 \times Tres.° \quad R \times Zb}{5.615 \times BPP \times 520} [62.37 \times live.oil.density - \quad (6)$$
$$dissolved.gas.density.at.BPP] + 62.37 \times live.oil.density$$

For this computation, input parameters may again be contamination corrected parameters. Live oil density may be obtained via in situ PVT measurements (pressure volume temperature measurements) or through other suitable measurements obtained via sensors such as sensors 139/160. The gas oil ratio (GOR) may be obtained from data collected by contamination monitoring module 152 and from the dissolved gas density obtained via Equation 5. The bubble point pressure (BPP) may be obtained from in situ PVT measurements. The Zb and Tres.° R also may be derived via Equation 5.

The second of the two independent methods used to determine the spread in FVF for oil at the bubble point pressure may be expressed as follows by Equation 7:

$$dead.oil.density = \left(\frac{141.5}{131.5 + API}\right)(62.37); \text{ in lb/ft}^3 \quad (7)$$

Where:

$$API = 80\log\left[\left(\frac{GOR}{gas.sp.gravity}\right)^{0.83}\left(\frac{18 \times 10^{9.1 \times 10^{-4} Tres.^\circ F}}{BPP}\right)\right]$$

$$gas.sp.gravity = \frac{\sum_{i=1}^{4} yiMi}{28.9};$$

(see Equation 5 for calculation of the mole fraction yi from weight fraction wi).

This second method is based on the Chevron method published in 1947 (see "The Technology of Artificial Lift Methods", Vol 1, p. 86, K. E. Brown, which contains the equation form of the Chevron API-BPP correlation; and see also "The Properties of Pet. Fluids", 2$^{nd}$ edition, p. 297, W. D. McCain Jr, which contains the graphical form of the Chevron API-BPP correlation). The Chevron method is used to estimate BPP using API gravity and other parameters. In the computational method described herein, the Chevron method may be used in the opposite sense in that knowing the contamination corrected BPP we are able to estimate API based on knowledge of other parameters. For example, API gravity may be estimated based on: BPP obtained from in situ PVT sensors 139; GOR; gas specific gravity derived from data obtained via contamination monitoring module 152; and pressure/temperature data. From the outputs of Equations 4, 5, 6, and 7, an output from Equation 3 may be obtained; and from the output of Equation 3, the Bob of Equation 2 may be determined. The Bob of Equation 1 is the single flash definition of Bob.

Furthermore, the Bo for P≥BPP can be obtained via Equation 8 as follows (at reservoir temperature):

$$Bo = Bob[1-(P-BPP)Co]; P \geq BPP \quad (8)$$

In Equation 8 above, Co (in 1/psi) is the coefficient of compressibility of oil under isothermal conditions and the value may be obtained from in situ PVT output, which uses density change with pressure to obtain the compressibility.

Additionally, the Bo for P≥BPP can be obtained via Equation 9 as follows:

$$Bo = 1 + (Bob - 1)\left(\frac{P}{BPP}\right); \quad (9)$$

$$P \leq BPP$$

A correction may be applied to Equation 9 above based on the coefficient of thermal expansion of the oil (thus unity becomes 1+[Tres−Tsurf][coeff.thermal.expansion]). This correction will be extremely small. It is also possible to infer a non-linear Bo below BPP using solution gas-oil-ratio (Rs) and not GOR. However, the uncertainties are generally inconsequential and do not warrant the correction. Accordingly, a linear drop of Bo from BPP to atmospheric pressure may be employed in the computational procedure.

In an operational example, appropriate input data is obtained in situ via sampling system 128 and associated sensors located downhole. The composition may comprise C1, C2, C3, C4, C5+ in weight percent hydrocarbons. As described herein, sampling system 128 may be used to determine the composition of a decontaminated sample of oil 148 via, for example, contamination monitoring module 152. If a contaminated composition were to be used, the FVF of the oil may be underestimated commensurate with the contamination, thus overestimating the oil-in-place. Because the composition of the oil samples 48 may be provided with greater granularity (e.g., C1, C2, C3, C4, C5, C6+), the composition can easily be converted to the above (C5+) format. The greater granularity may be useful for application of a primary tuning parameter (e.g., partition coefficient). It should be noted that if the composition of the oil sample is provided in mole percent (e.g., if published lab data is to be analyzed via the computational procedure provided herein) the molecular weight of the lumped or pseudo-component may be used.

The sampling system 128 also may be used to obtain other input data such as contamination corrected properties (e.g., BPP, GOR, live oil density). Pressure data also may be used if the live oil density is not measured at bubble point pressure. Temperature at which the bubble point pressure is measured also may be added to the input data along with Co (compressibility).

Figure 8:
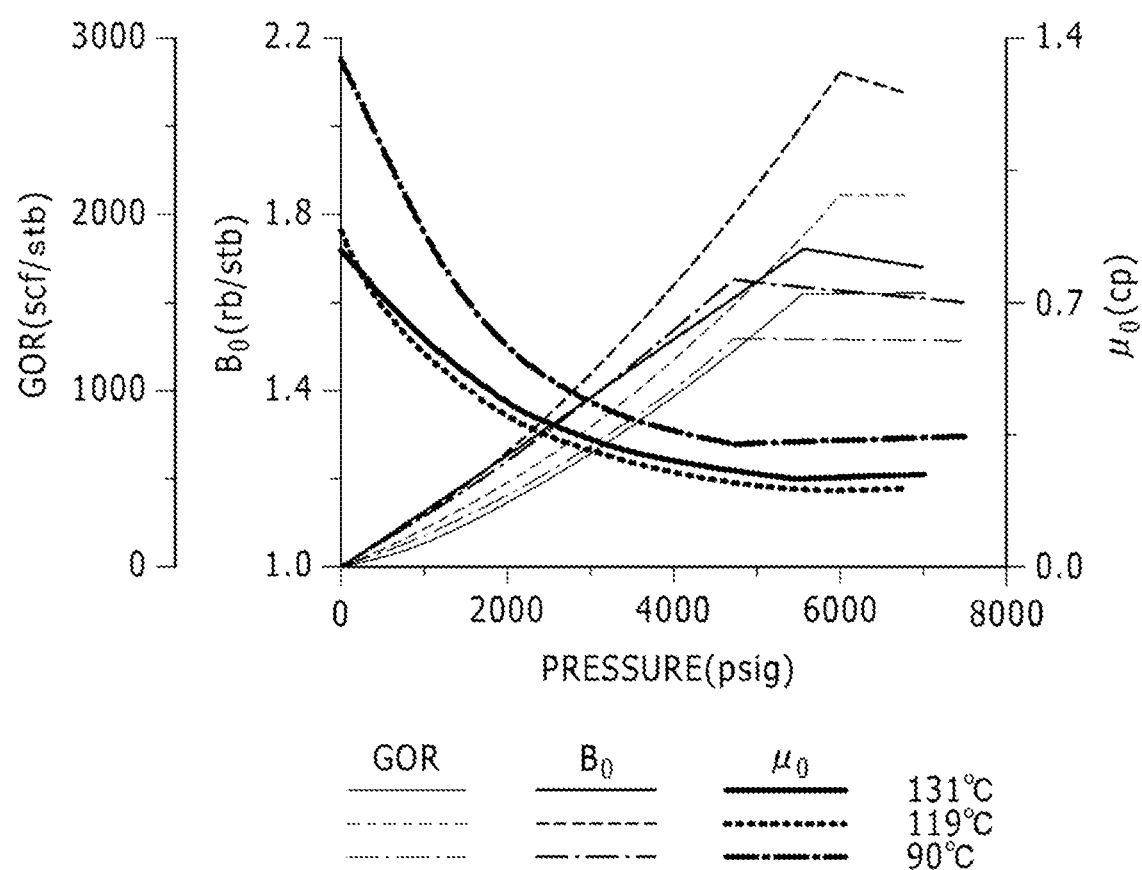
FIG. 8 is a graphical illustration showing another example of formation volume factor behavior versus reservoir pressure, according to an embodiment of the disclosure.

Referring generally to FIG. 8, a graphical example is provided of FVF of oil (Bo) from a first oil field (solid line) and from two other oil fields (dashed lines). The graphical example was derived based on the computational technique described herein. In this specific example, the data subjected to the computational procedure to provide the formation volume factor (Bo) over a range of pressures was determined based on the following data:

Composition [C1, C2, C3, C4, C5+] in wt %: 10.38, 1.00, 0.80, 0.50, 87.32;

GOR=1600 scf/STB; BPP=5400 psi; API=36 (so no live oil density is used in this case); gas sp. gravity=0.68 (matching this gave the distribution of C1 to C4); T=131° C.=268° F.=728° R; Bob=1.72 RB/STB; compressibility (not given, though can be inferred from the negative slope); here we can compute Bob;

Dissolved gas mass fraction =

$$\sum_{i=1}^{4} wi = 0.1038 + 0.0100 + 0.0080 + 0.0050 = 0.1268;$$

Dead oil mass fraction=1−0.1268=0.8732;
Dead oil density (obtained directly from API gravity)= [141.5/(131.5+36)]*62.37=52.7 lb/ft3;
Dissolved gas density at BPP=(5400*0.68*28.9)/ (1.1*10.73*728)=12.4 lb/ft$^3$; Zb is taken to be 1.1; and Bob=1.0+(0.1268/0.8732)(52.7/12.4)=1.62 RB/STB (i.e. 1.62 reservoir barrels/stock tank barrels).

Such data may be obtained via sampling system 128 and via appropriate processing of the data obtained via sampling system 128 according to the equations described above.

Depending on the parameters of a given application and/or environment, the sampling system 128 may comprise a variety of structures and components. For example, the sampling system 128 may comprise various modules for obtaining the desired data used to enable the downhole fluid analysis and the computational procedure described herein. In some embodiments, the sampling system 128 comprises contamination monitoring module 152 to facilitate determination of a decontaminated oil sample. Additionally, the contamination monitoring module 152 may comprise a variety of sensors able to obtain the desired data for processing to effectively determine a contamination corrected oil sample.

Similarly, the microfluidic module 154 may comprise a variety of sensors to obtain the desired data used to compute the FVF of the oil and/or other desired properties. Module 152 and/or module 154 may comprise or may work in cooperation with pressure and temperature sensors 139. The sampling system 28 also may be used with a variety of well strings 134 and other well systems. The data obtained and analyzed via sampling system 128 may be further processed according to the algorithms and computational methodology described herein at a suitable downhole and/or surface location.

Figure 9:
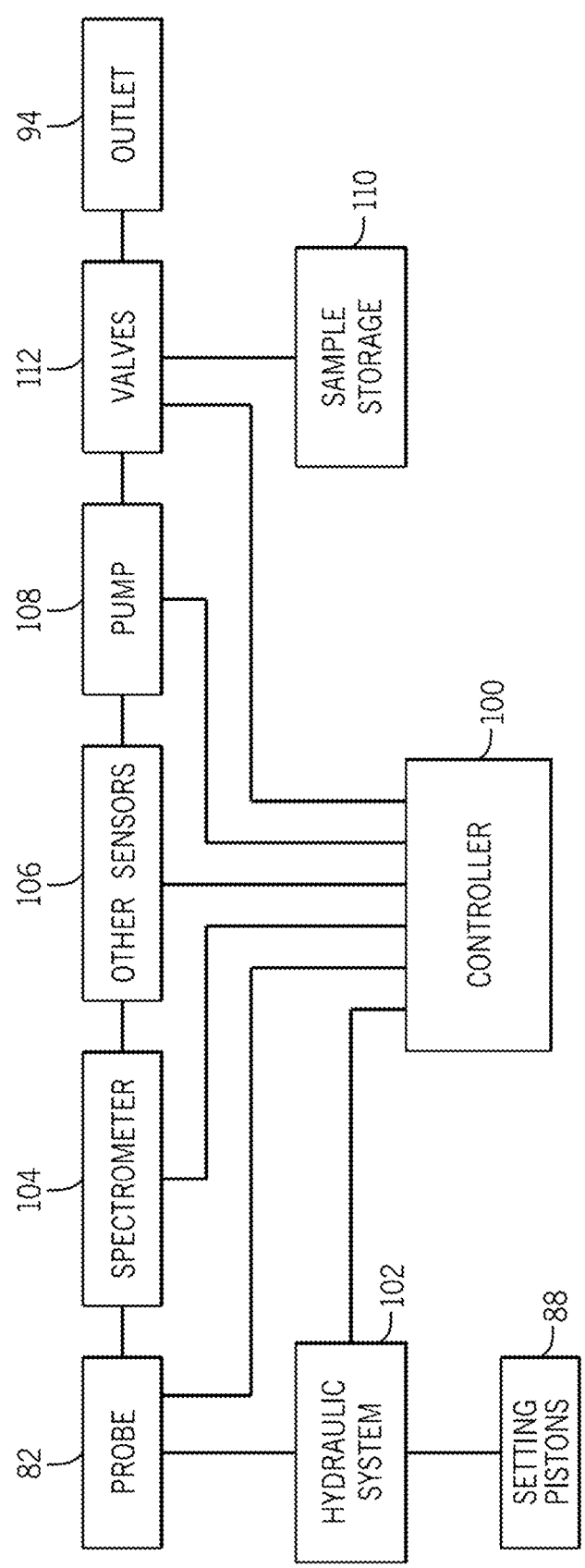
FIG. 9 is a block diagram of components of a fluid sampling tool operated by a controller in accordance with an embodiment of the present disclosure.

Additional details as to the construction and operation of the fluid sampling tool 62 may be better understood through reference to FIG. 9. As shown in this figure, various components for carrying out functions of the fluid sampling tool 62 can be connected to a controller 100. The various components can include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94. The controller 100 may include or be coupled to an operator interface (not shown) that provides logs of predicted formation fluid properties that are accessible to an operator.

In operation, the hydraulic system 102 can extend the probe 82 and the setting pistons 88 to facilitate sampling of a formation fluid through the wall 84 of the well 14. It also can retract the probe 82 and the setting pistons 88 to facilitate subsequent movement of the fluid sampling tool 62 within the well. The spectrometer 104, which can be positioned within the fluid analyzer 72, can collect data about optical properties of the sampled formation fluid. Such measured optical properties can include optical densities (absorbance) of the sampled formation fluid at different wavelengths of electromagnetic radiation. Using the optical densities, the composition of a sampled fluid (e.g., volume fractions of its constituent components) can be determined. Other sensors 106 can be provided in the fluid sampling tool 62 (e.g., as part of the probe module 70 or the fluid analyzer 72) to take additional measurements related to the sampled fluid. In various embodiments, these additional measurements could include reservoir pressure and temperature, live fluid density, live fluid viscosity, electrical resistivity, saturation pressure, and fluorescence, to name several examples. In some embodiments, as mentioned above, some or all of other sensors 106 may be incorporated into a DFA module (e.g., such as in a PVT unit) of the fluid sampling tool 62. Other characteristics, such as gas-to-oil ratio (GOR), may also be determined using the DFA measurements.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 9, the controller 100 can facilitate operation of the fluid sampling tool 62 by controlling various components. Specifically, the controller 100 can direct operation (e.g., by sending command signals) of the hydraulic system 102 to extend and retract the probe 82 and the setting pistons 88 and of the pump 108 to draw formation fluid samples into and through the fluid sampling tool. The controller 100 can also receive data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 can also operate the valves 112 to divert sampled fluids from the flowline 92 into the storage devices 110.

The various fluid properties mentioned above and measured by the tools described herein may be affected by OBM filtrate contamination in the sampled fluid (referred to as "contaminated" fluid). For example, measured saturation pressures, such as measured by a downhole PVT unit of a DFA module, may be affected by OBM filtrate contamination and may not accurately reflect the saturation pressure of the uncontaminated fluid. The saturation pressures may increase or decrease with an increase in OBM filtrate contamination.

By way of example, FIGS. 10-12 depict plots of saturation pressure vs. OBM filtrate contamination (as a volume fraction expressed as percentage) data points indicating a relationship between saturation pressures, such as bubble point pressure or dew point pressure, and OBM filtrate contamination. FIG. 10 depicts a plot 400 of the bubble point pressure of heavy oil vs. volume fraction of various OBM filtrate contaminates (esters, mineral oil, and olefins). FIG. 11 depicts a plot 500 of measured bubble point pressure of black oil vs. volume fraction of various OBM filtrate contaminates (esters, mineral oil, and olefins). Similarly, FIG. 12 depicts a plot 600 of measured dew point pressure of gas condensate vs. volume fractions of various OBM filtrate contaminates (esters, mineral oil, and olefins). As shown in FIGS. 10-12, for an OBM filtrate contamination below a certain amount, the bubble point and dew point pressures are approximately a linear function of the OBM filtrate contamination, regardless of whether the bubble point and dew point increase or decrease relative to increased OBM filtrate contamination. In some embodiments, as shown in FIGS. 10-12, a linear function may be used to approximate the relationship between saturation pressure and OBM filtrate contaminations below about 40% volume. However, it should be appreciated that the slope of each linear approximation function varies with the composition of the OBM filtrate and the composition of the fluid. Thus, in other embodiments, a linear function may be used to approximate the relationship between saturation pressure and OBM filtrate contaminations about 10% volume or less, 20% volume or less, 30% volume or less, 40% volume or less, or other suitable OBM contamination obtained from saturation pressure and OBM filtrate contamination data.

In view of the linear function approximations discussed above, the saturation pressure of a contaminated fluid may be expressed as follows by Equation 10:

$$P^{sat} = v_{obm} P_{obm}^{hypo} + (1 - v_{obm}) P_0^{sat} \qquad (10)$$

Where, $P^{sat}$ is the saturation pressure of the contaminated fluid, $v_{obm}$ is the OBM filtrate contamination in volume fraction of the contaminated fluid as measured by a downhole tool, $P_0^{sat}$ is the saturation pressure of the uncontaminated (also referred to as "native") fluid, and $P_{obm}^{hypo}$ is the hypothetical OBM filtrate saturation pressure. The hypothetical OBM filtrate saturation pressure may be used instead of the real OBM filtrate saturation pressure; because no gas is dissolved and the OBM filtrate is typically heavier than $C_7$, the real OBM filtrate saturation pressure is nearly zero. Additionally, using the hypothetical OBM filtrate saturation enables use of a linear function over a linear range of contamination, as the relationship of saturation pressure to OBM filtrate contamination may be non-linear at higher contamination.

By factoring $v_{obm}$, Equation 10 may be rewritten as Equation 11 below:

$$P^{sat} = (P_{obm}^{hypo} - P_0^{sat})v_{obm} + P_0^{sat} \quad (11)$$

As mentioned, at relatively low OBM filtrate contamination, the saturation pressure is a linear function of OBM filtrate contamination. The slope of the line of such a linear function is $P_{obm}^{hypo} - P_0^{sat}$ and the y-axis intercept at a value of zero OBM filtrate concentration is $P_0^{sat}$. Thus, as described herein, saturation pressures may be measured during cleanup at different OBM filtrate contamination levels and the linear relationship may be approximated by Equation 11 and used to obtain the $P_0^{sat}$ of the uncontaminated fluid.

Figure 13:
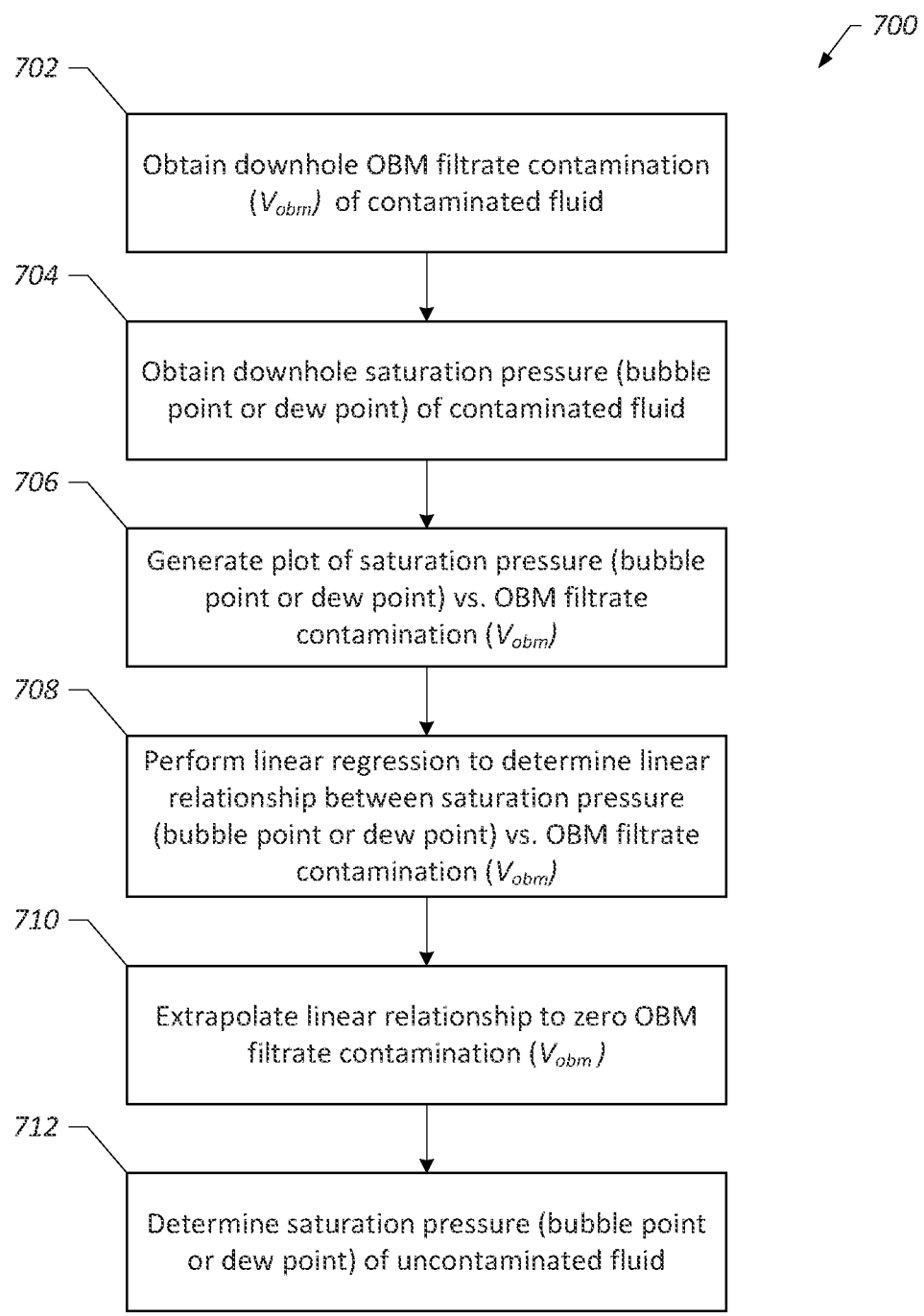
FIG. 13 is a block diagram of a process for determining saturation pressure of an uncontaminated fluid in accordance with an embodiment of the present disclosure.

FIG. 13 depicts a process for determining the saturation pressure (bubble point pressure or dew point pressure) of an uncontaminated fluid in accordance with the techniques described herein. The process may be performed using a downhole tool having a DFA module, such as that described above. As will be appreciated, the determination described in process 700 is executed on a downhole fluid sample, thus eliminating the need to preserve fluid samples and transport samples to the surface and, in some instances, to a laboratory for further analysis. The downhole fluid sample may be obtained by initiating a pumpout of contaminated fluid, such as during cleanup of a well.

Downhole OBM filtrate contamination ($v_{obm}$) may be obtained (block 702) by various suitable techniques. In some embodiments, properties such as optical density, gas/oil ratio, mass density, pumpout volume, pumpout time, and the like may be measured during pumpout and cleanout using a DFA apparatus. In such embodiments, OBM filtrate concentration may be determined by DFA OBM filtrate concentration (OCM) techniques, such as those described in U.S. Pat. Nos. 6,956,204 and 8,204,125. In some embodiments, the OBM filtrate concentration may be determined according to the techniques described in U.S. application Ser. No. 14/085,589, entitled "Method and Apparatus for Consistent and Robust Fitting in Oil-Based Mud Filtrate Contamination Monitoring for Multiple Downhole Sensors", now U.S. Pat. No. 10,316,655, a copy of which is herein incorporated by reference. Next, downhole saturation pressure measurements of the contaminated fluid may be obtained (block 704). In some embodiments, downhole saturation pressure measurements may be obtained using a downhole PVT unit of a DFA module.

In some embodiments, the additional operations of process 700 may be performed after a threshold OBM filtrate contamination is reached. In such embodiments, OBM filtrate contamination may be continuously determined during pumpout of the contaminated fluid until sufficient fluid has been pumped to reach a desired OBM filtrate contamination. For example, in some embodiments the additional operations of the process 700 may be performed after a threshold OBM filtrate contamination of about 10% volume or less, 20% volume or less, 30% volume or less, 40% volume or less, or other suitable OBM contamination volume.

Next, a plot of the measured downhole saturation pressures vs. OBM filtrate contamination may be generated (block 706). As discussed above, in some embodiments the bubble point pressure or the dew point pressure may be plotted against the determined volume fraction of OBM filtrate contamination. Next, a linear regression may be performed on the data points of the plot to determine the linear relationship between the measured saturation pressures and the OBM filtrate contamination (block 708). As discussed above, the linear relationship may be expressed according to Equation 11 and the slope of the linear function may be $P_{obm}^{hypo} - P_0^{sat}$.

Next, the linear relationship may be extrapolated to a zero OBM filtrate contamination (block 710) (e.g., a y-axis intercept), and the saturation pressure (bubble point pressure or dew point pressure) of the uncontaminated fluid may be determined (block 712). As will be appreciated, the process 700 described above may be performed for bubble point pressures or dew point pressures measured downhole.

Although the embodiments described above discuss determination of a linear relationship between saturation pressure and OBM filtrate contamination for certain volume fractions of OBM filtrate contamination, it should be appreciated that the linear relationship and linear function are provided by way of example and other embodiments may include a non-linear relationship. For example, some fluids and OBM mixtures may exhibit a non-linear relationship between saturation pressure and OBM filtrate contamination. In such embodiments, a polynomial or other non-linear function may be determined from a plot of saturation pressure vs. OBM filtrate contamination volume fraction, and the process 700 described above may be performed using a non-linear function instead of the linear function. Thus, in the manner described above, the non-linear function may be extrapolated to zero OBM filtrate to determine the saturation pressure of the uncontaminated fluid.

Figure 14:
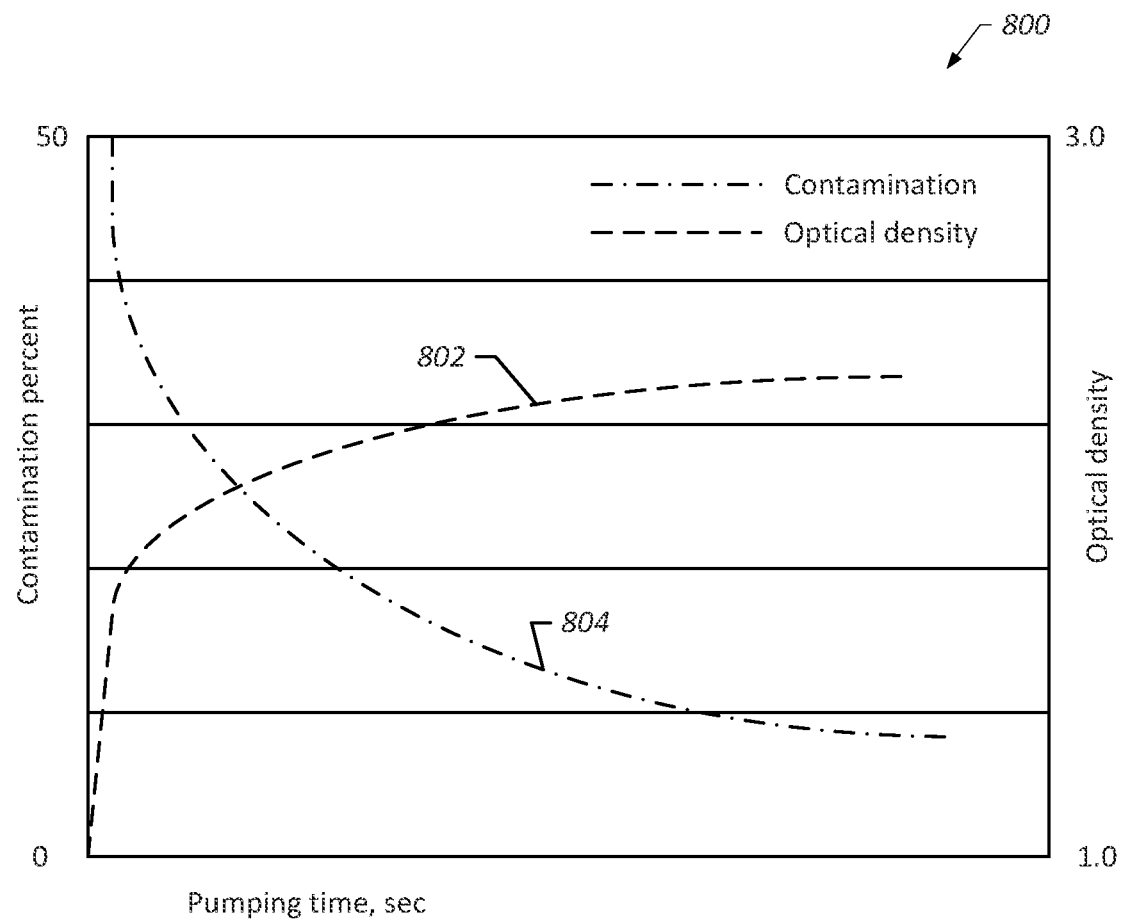
FIG. 14 is a plot of optical density and OBM filtrate contamination vs. pumping time in accordance with an embodiment of the present disclosure.
Figure 15:
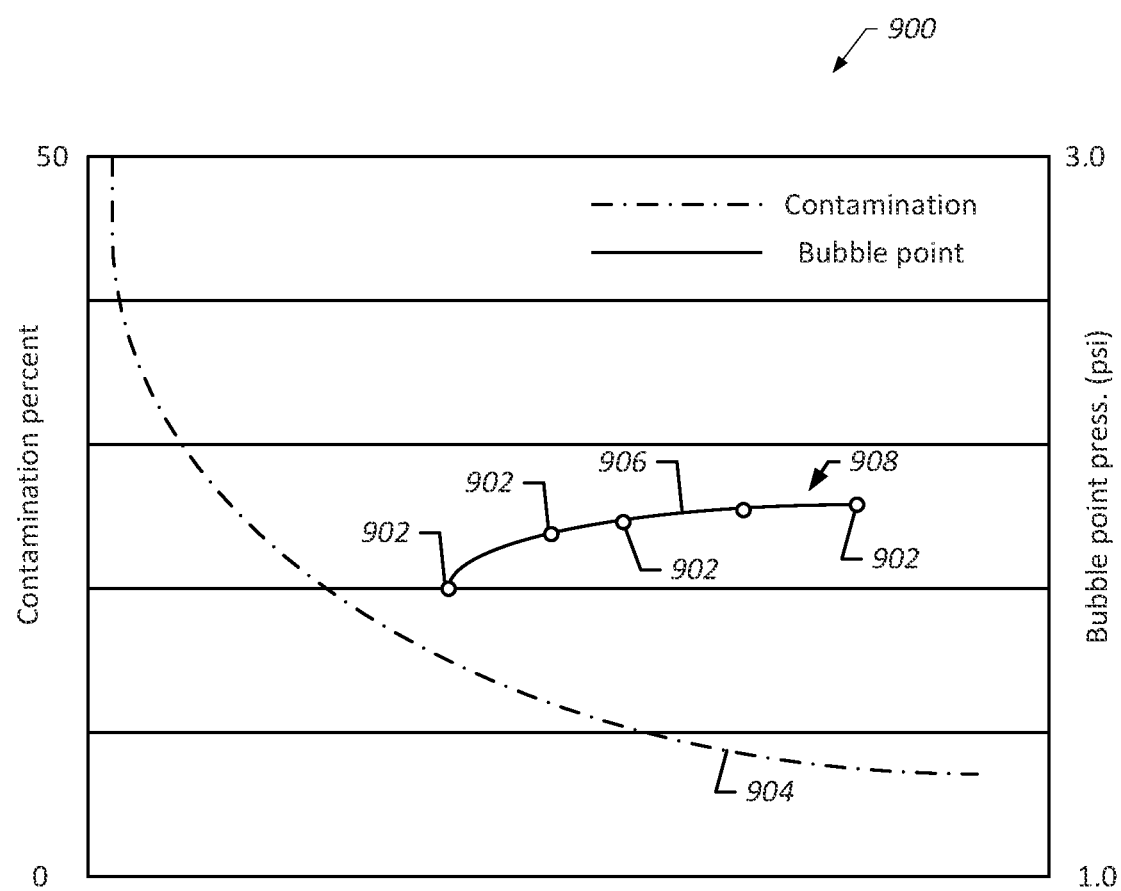
FIG. 15 is plot of measured bubble point pressures and OBM filtrate contamination vs. pumping time in accordance with an embodiment of the present disclosure.
Figure 16:
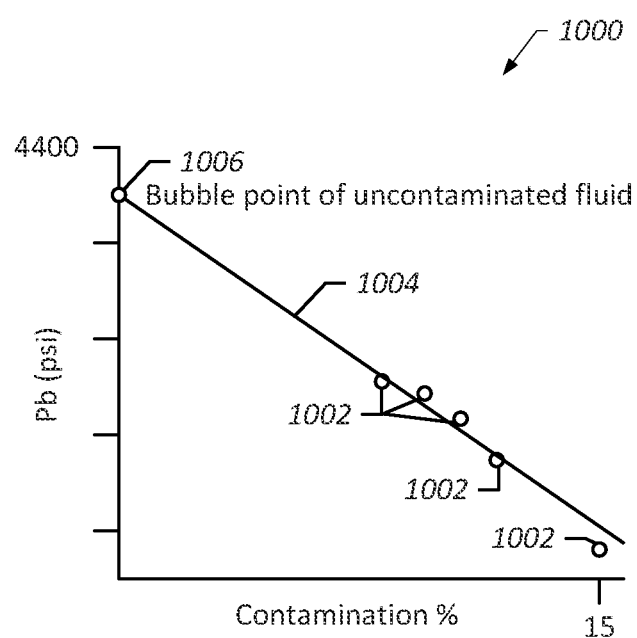
FIG. 16 is a plot of a linear function for measured bubble point pressures vs. OBM filtrate contamination in accordance with an embodiment of the present disclosure.

FIGS. 14-16 depict different plots illustrating an example of the techniques described above for determining saturation pressure of an uncontaminated fluid. FIG. 14 depicts a plot 800 of optical density (as measured using a DFA module) 802 and OBM filtrate contamination 804 as a function of pumping time during a downhole cleanup process for crude oil. As shown in the plot 800, the optical density decreases 802 with time. After the OBM filtrate contamination reaches a certain level, downhole saturation pressures may begin to be measured using, for example, a DFA module. FIG. 15 depicts a plot 900 of measured bubble point pressures 902 and OBM filtrate contamination 904 as a function of pumping time. As shown in FIG. 15, the bubble point pressure increases as the pumping time increases; however, the bubble point pressure curve 906 begins to flatten out as the pumping time increases, as illustrated by portion 908.

FIG. 16 depicts a plot 1000 of data points 1002 of measured bubble point pressure vs. OBM filtrate contamination, such as described above in block 708. As shown in FIG. 14, a linear regression may be used to determine a linear relationship (e.g., linear function 1004) for the data points 1002. As mentioned above, the slope of the line of the linear relationship 1004 may be $P_{obm}^{hypo} - P_0^{sat}$. The linear relationship 1004 may be extrapolated to zero OBM filtrate contamination (e.g., to intercept the y-axis of the plot 1000), as illustrated by point 1006 in FIG. 16. The bubble point pressure of the uncontaminated fluid may be determined at point 1006 (e.g., approximately 4375 psi).

In some embodiments, the flatness of the saturation pressure curve may be used as indication of OBM filtrate contamination. For example, as depicted in FIG. 14, as pumping time increases, the bubble point pressure curve 906 flattens out, as shown by portion 908. If the bubble point pressure curve 906 is flat (or its derivative is zero), the OBM filtrate contamination may be equal to or nearly zero.

In some embodiments, the OBM filtrate contamination may be determined using an observed bubble point pressure curve during a pumpout. Equation 10 described above may be rewritten to determine OBM filtrate contamination, as expressed below in Equation 12:

$$v_{obm} = \alpha \frac{P_0^{sat} - P^{sat}}{P_0^{sat} - P_{obm}^{hypo}} \quad (12)$$

Where $P^{sat}$ is the saturation pressure of the contaminated fluid as measured downhole (e.g., via a DFA apparatus), $P_{obm}^{hypo}$ is the hypothetical OBM saturation pressure and may be assumed to be equal to zero for crude oil or, in some embodiments, may be an adjusted parameter based on the fluid and OBM filtrate, $P_0^{sat}$ is the saturation pressure of the uncontaminated fluid, and $\alpha$ is a constant that depends on the properties of the OBM filtrate and the reservoir fluid. In some embodiments, $\alpha$ may be assumed to 1. In other embodiments, $\alpha$ may be determined from another fluid property that follows a lever rule, such as density. For example, in such embodiments, a may be calculated from the volume contamination from the density at two points and the relative contamination from the bubble point pressure at two points. The measured $P^{sat}$ may be fitted using the power function described below in Equation 13:

$$P^{sat} = P_0^{sat} - \beta V^{-\gamma} \quad (13)$$

Where V is the measured pumpout volume (e.g., as measured by a DFA module) and $P_0^{sat}$, $\beta$ and $\gamma$, are adjustable parameters. In some embodiments, the power function described in Equation 13 may be expressed using the pumpout time t to replace the measured pumpout volume V. In other embodiments, other function for the saturation pressure may be fitted.

Figure 17:
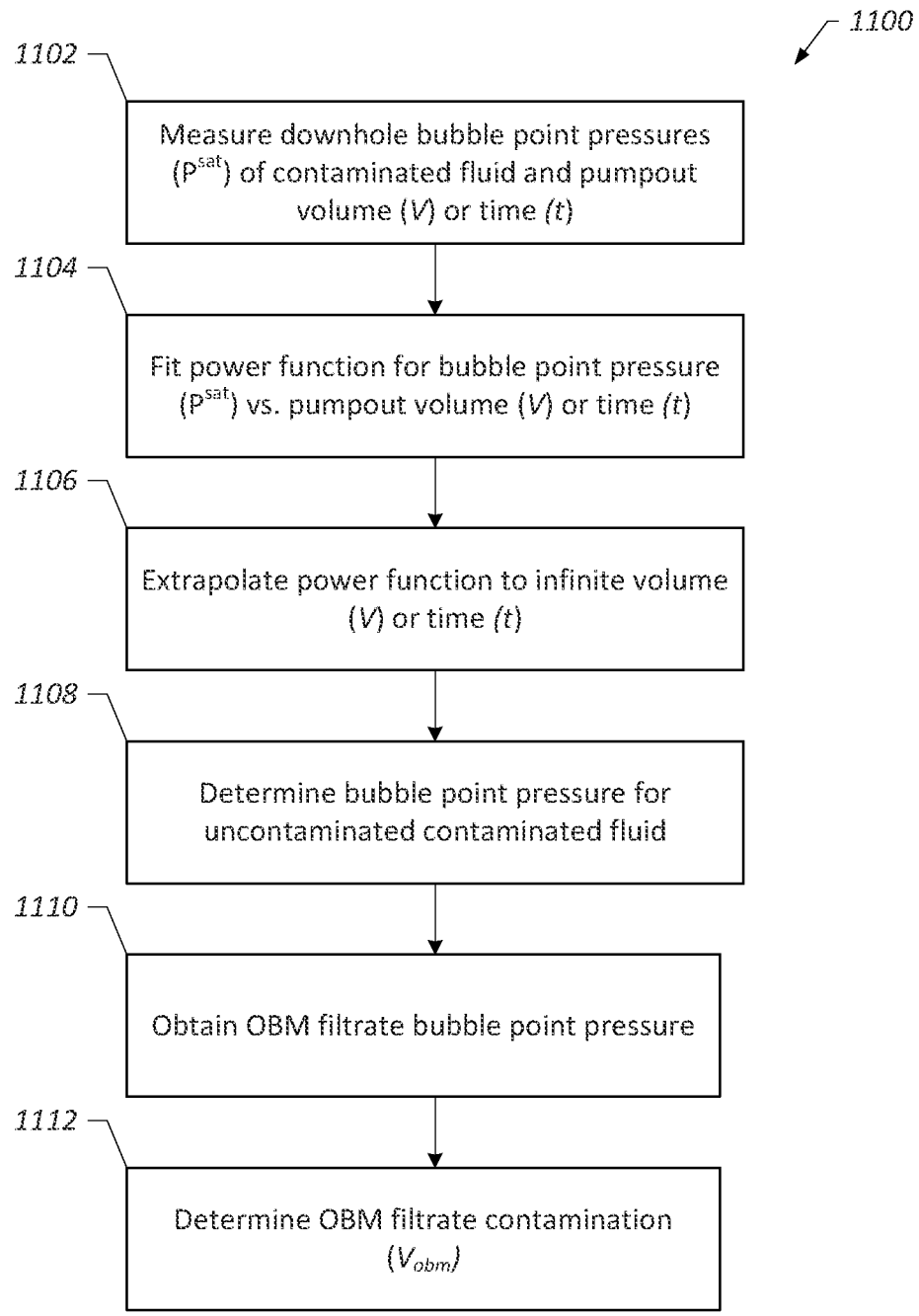
FIG. 17 is a block diagram of a process for determining OBM filtrate contamination from measured bubble point pressures in accordance with an embodiment of the present disclosure.

FIG. 17 depicts a process 1100 for determining OBM filtrate contamination based on measured downhole bubble point pressures in accordance with an embodiment of the present technique. The process may be performed using a downhole tool having a DFA module, such as the tools described above. As will be appreciated, the determination described in process 1100 is executed on a downhole fluid sample, thus eliminating the need to preserve fluid samples and transport samples to the surface and, in some instances, to a laboratory for further analysis.

Initially, downhole bubble point pressures of a fluid and pumpout volume or time may be measured (block 1102) during pumpout of contaminated fluid, such as during cleanup of a well. Next, the power function for bubble point pressure as a function of pumpout volume, as described by Equation 13, may be fitted to the measured bubble point pressure curve (block 1104). In other embodiments, as mentioned above, the pumpout time t may be used instead of the pumpout volume V and a corresponding power function of bubble point pressure as a function of pumpout time t may be fitted.

Next, the fitted power function may be extrapolated to infinite volume V, or, in some embodiments, infinite time t (block 1106), and the bubble point pressure for the uncontaminated fluid may be determined from the bubble point pressure at infinite volume V or infinite time t (block 1108). As described above, the OBM filtrate bubble point pressure may be obtained (block 1111). In some embodiments, the OBM filtrate bubble point pressure may be assumed to equal zero. In other embodiments, the OBM filtrate bubble point pressure may be obtained by fitting data obtained from another source, such as another well using the OBM filtrate. In other embodiments, the OBM filtrate bubble point pressure may be the hypothetical OBM filtrate saturation pressure, as described. Next, the OBM filtrate contamination may be determined using Equation 12 (block 1112). In some embodiments, the OBM filtrate contamination may be monitored to obtain a desired sample of the fluid in a downhole tool.

Figure 18:
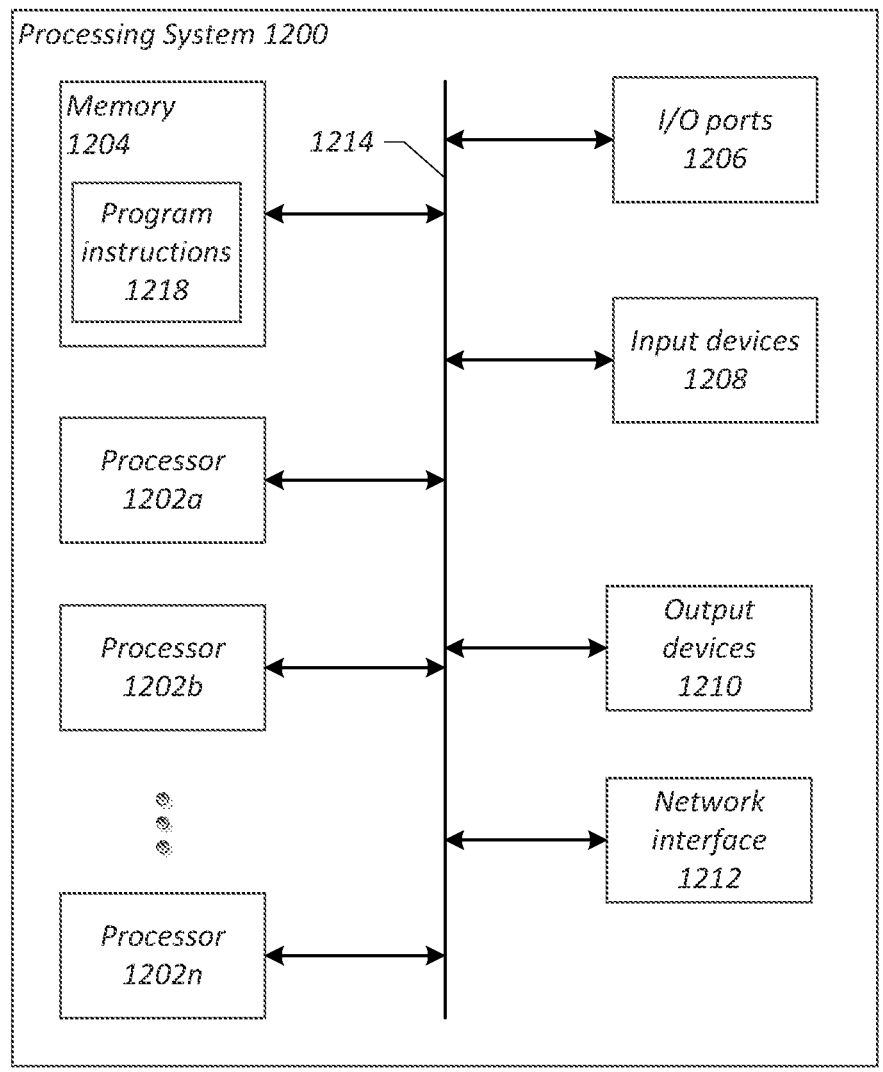
FIG. 18 is a block diagram of a processing system in accordance with an embodiment of the present disclosure.

FIG. 18 is a block diagram of an example processing system 1200 that may execute example machine-readable instructions used to implement one or more of processes described herein and, in some embodiments, to implement a portion of one or more of the example downhole tools described herein. The processing system 1000 may be or include, for example, controllers (e.g., controller 100), special-purpose computing devices, servers, personal computers, personal digital assistant (PDA) devices, tablet computers, wearable computing devices, smartphones, internet appliances, and/or other types of computing devices. Moreover, while it is possible that the entirety of the system 1200 shown in FIG. 18 is implemented within a downhole tool, it is also contemplated that one or more components or functions of the system 1200 may be implemented in wellsite surface equipment. As shown in the embodiment illustrated in FIG. 18, the processing system 1200 may include one or more processors (e.g., processors 1202A-1202N), a memory 1204, I/O ports 1206 input devices 1208, output devices 1210, and a network interface 1214. The process system 1200 may also include one or more additional interfaces 1214 to facilitate communication between the various components of the system 1200.

The processor 1202 may provide the processing capability to execute programs, user interfaces, and other functions of the system 1200. The processor 1202 may include one or more processors and may include "general-purpose" microprocessors, special purpose microprocessors, such as application-specific integrated circuits (ASICs), or any combination thereof. In some embodiments, the processor 1202 may include one or more reduced instruction set (RISC) processors, such as those implementing the Advanced RISC Machine (ARM) instruction set. Additionally, the processor 1202 may include single-core processors and multicore processors and may include graphics processors, video processors, and related chip sets. Accordingly, the system 1200 may be a uni-processor system having one processor (e.g., processor 1202a), or a multi-processor system having two or more suitable processors (e.g., 1202A-1202N). Multiple processors may be employed to provide for parallel or sequential execution of the techniques described herein. Processes, such as logic flows, described herein may be performed by the processor 1202 executing one or more computer programs to perform functions by operating on input data and generating corresponding output. The processor 1202 may receive instructions and data from a memory (e.g., memory 1204).

The memory 1204, which may include one or more tangible non-transitory computer readable storage mediums, may include volatile memory and non-volatile memory accessible by the processor 1202 and other components of the system 1200. For example, the memory 1204 may include volatile memory, such as random access memory (RAM). The memory 1204 may also include non-volatile memory, such as ROM, flash memory, a hard drive, other suitable optical, magnetic, or solid-state storage mediums or any combination thereof. The memory 1204 may store a variety of information and may be used for a variety of purposes. For example, the memory 1204 may store executable computer code, such as the firmware for the system 1200, an operating system for the system 1200, and any other programs or other executable code for providing functions of the system 1200. Such executable computer code may include program instructions 1218 executable by a processor (e.g., one or more of processors 1202A-1202N) to implement one or more embodiments of the present disclosure. Program instructions 1218 may include computer program instructions for implementing one or more techniques described herein. Program instructions 1218 may include a computer program, which in certain forms is known as a program, software, software application, script, or code.

The interface 1214 may include multiple interfaces and may enable communication between various components of the system 1200, the processor 1202, and the memory 1204. In some embodiments, the interface 1214, the processor 1202, memory 1204, and one or more other components of the system 1200 may be implemented on a single chip, such as a system-on-a-chip (SOC). In other embodiments, these components, their functionalities, or both may be implemented on separate chips. The interface 1214 may enable communication between processors 1202a-1202n, the memory 1204, the network interface 1210, or any other devices of the system 1200 or a combination thereof. The interface 1214 may implement any suitable types of interfaces, such as Peripheral Component Interconnect (PCI) interfaces, the Universal Serial Bus (USB) interfaces, Thunderbolt interfaces, Firewire (IEEE-1394) interfaces, and so on.

The system 1200 may also include an input and output port 1208 to enable connection of additional devices, such as I/O devices 1214. Embodiments of the present disclosure may include any number of input and output ports 1208, including headphone and headset jacks, universal serial bus (USB) ports, Firewire (IEEE-1394) ports, Thunderbolt ports, and AC and DC power connectors. Further, the system 1200 may use the input and output ports to connect to and send or receive data with any other device, such as other portable computers, personal computers, printers, etc.

The processing system 1200 may include one or more input devices 1208. The input device(s) 1208 permit a user to enter data and commands used and executed by the processor 1212. The input device 1208 may include, for example, a keyboard, a mouse, a touchscreen, a track-pad, a trackball, an isopoint, and/or a voice recognition system, among others. The processing system 1200 may also include one or more output devices 1210. The output devices 1210 may include, for example, display devices (e.g., a liquid crystal display or cathode ray tube display (CRT), among others), printers, and/or speakers, among others.

The system 1200 depicted in FIG. 18 also includes a network interface 1210. The network interface 1210 may include a wired network interface card (NIC), a wireless (e.g., radio frequency) network interface card, or combination thereof. The network interface 1210 may include known circuitry for receiving and sending signals to and from communications networks, such as an antenna system, an RF transceiver, an amplifier, a tuner, an oscillator, a digital signal processor, a modem, a subscriber identity module (SIM) card, memory, and so forth. The network interface 1210 may communicate with networks (e.g., network 1216), such as the Internet, an intranet, a cellular telephone network, a wide area network (WAN), a local area network (LAN), a metropolitan area network (MAN), or other devices by wired or wireless communication using any suitable communications standard, protocol, or technology.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language is not generally intended to imply that features, elements, and/or operations are in any way used for one or more implementations or that one or more implementations necessarily include logic for deciding, with or without user input or prompting, whether these features, elements, and/or operations are included or are to be performed in any particular implementation.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense and not for purposes of limitation.

What is claimed is:

1. A method for downhole fluid analysis, comprising:
deploying a sampling system downhole in a borehole located within a reservoir containing hydrocarbons;
using the sampling system to obtain contaminated fluid samples at a plurality of stations along the borehole, the contaminated fluid samples containing fluid and oil based mud (OBM) filtrate;
providing a processor with at least one property of the contaminated fluid samples;
analyzing each contaminated fluid sample in situ to determine saturation pressure and density of each contaminated fluid sample;
correcting for any oil based mud (OBM) filtrate;
determining the saturation pressure of each fluid of the contaminated fluid sample; and
further comprising determining a formation volume factor (FVF) of oil in the reservoir based on saturation pressure and density of the fluid.

2. The method as recited in claim 1, wherein analyzing comprises using a contamination monitoring module of the sampling system.

3. The method as recited in claim 2, wherein further analyzing comprises using a microfluidic measurement module.

4. The method as recited in claim 3, wherein using the contamination monitoring module comprises using an optical spectroscopy sensor, a viscosity sensor, and a density sensor.

5. The method as recited in claim 4, wherein using the microfluidic measurement module comprises placing each oil sample in a depressurization chamber.

6. The method as recited in claim 1, wherein processing comprises determining variations in FVF as the pressure on the oil varies from an initial reservoir pressure to a bubble point pressure.

7. The method as recited in claim 1, wherein further analyzing comprises incipient flashing of each contaminated fluid sample within the borehole.

8. A method, comprising:
obtaining a contaminated fluid sample from a reservoir at a downhole location in a borehole, the contaminated fluid sample containing fluid and oil based mud filtrate;

providing a processor with at least one property of the contaminated fluid sample; and using a contamination monitoring module and sensors at the downhole location to obtain data on the fluid; and processing the data obtained downhole to determine an FVF of oil in the reservoir.

9. The method as recited in claim 8, wherein obtaining comprises obtaining a plurality of contaminated fluid samples at a plurality of stations along the borehole wherein the fluid is oil.

10. The method as recited in claim 8, wherein using comprises using the sensors in the contamination monitoring module to determine optical spectroscopy, viscosity, and density of the oil.

11. The method as recited in claim 8, wherein using comprises using the sensors to determine optical spectroscopy, viscosity, and density of the oil.

12. The method as recited in claim 8, wherein using further comprises depressurizing the contaminated sample in a depressurization chamber to determine bubble point pressure.

13. The method as recited in claim 8, wherein processing comprises processing the data at a downhole location.

14. The method as recited in claim 8, wherein processing comprises using the FVF to determine original oil-in-place in a geological structure.

15. The method as recited in claim 8, wherein processing comprises determining variations in the FVF from initial reservoir pressure to bubble point pressure.

16. A system, comprising:
a well string comprising a sampling system deployed downhole in a wellbore, the sampling system comprising a contamination monitoring module;
a processor configured to process the data; and
a non-transitory tangible machine-readable memory coupled to the processor, the non-transitory tangible machine-readable memory storing machine-readable instructions that when executed by the processor cause the processor to perform operations comprising:
measuring downhole saturation pressures of a contaminated fluid over a pumpout volume or a pumpout time, wherein the contaminated fluid comprises fluid and OBM filtrate;
determining a function for the measured saturation pressures based on the pumpout volume or pumpout time;
extrapolating the function to infinite pumpout volume or infinite pumpout time;
determining a saturation pressure for the fluid at the infinite pumping volume or infinite pumping time;
obtaining a saturation pressure of the fluid; and
processing the data obtained downhole to determine an FVF of oil in the reservoir.

17. The system as recited in claim 16, wherein the downhole saturation pressure comprises bubble point pressures.

18. The system as recited in claim 16, wherein the operations further comprise determining the FVF of the uncontaminated fluid based on the downhole saturation pressure and a density of the uncontaminated fluid.

* * * * *